(12) United States Patent
Burke et al.

(10) Patent No.: US 11,127,485 B2
(45) Date of Patent: Sep. 21, 2021

(54) TECHNIQUES FOR FINE GRAINED CORRECTION OF COUNT BIAS IN MASSIVELY PARALLEL DNA SEQUENCING

(71) Applicant: Echelon Diagnostics, Inc., Reno, NV (US)

(72) Inventors: John Burke, Reno, NV (US); Brian Rhees, Tracy, CA (US)

(73) Assignee: ECHELON DIAGNOSTICS, INC., Reno, NV (US)

( * ) Notice: Subject to any disclaimer, the term of this patent is extended or adjusted under 35 U.S.C. 154(b) by 1030 days.

(21) Appl. No.: 15/717,152

(22) Filed: Sep. 27, 2017

(65) Prior Publication Data

US 2018/0089367 A1 Mar. 29, 2018

Related U.S. Application Data

(60) Provisional application No. 62/400,610, filed on Sep. 27, 2016.

(51) Int. Cl.
| | | |
|---|---|---|
| G16B 30/00 | (2019.01) | |
| C12Q 1/6874 | (2018.01) | |
| G01N 33/48 | (2006.01) | |
| G16B 25/00 | (2019.01) | |
| G16B 20/00 | (2019.01) | |
| G16B 20/10 | (2019.01) | |
| G16B 30/10 | (2019.01) | |

(52) U.S. Cl.
CPC .......... *G16B 30/00* (2019.02); *C12Q 1/6874* (2013.01); *G01N 33/48* (2013.01); *G16B 20/00* (2019.02); *G16B 20/10* (2019.02); *G16B 25/00* (2019.02); *G16B 30/10* (2019.02); *C12Q 2521/501* (2013.01); *C12Q 2565/102* (2013.01)

(58) Field of Classification Search
None
See application file for complete search history.

(56) References Cited

PUBLICATIONS

Boeva et al. Bioinformatics vol. 27, pp. 268-269 and supplemental content (Year: 2011).*

Chen, S., et al.. "A method for noninvasive detection of fetal large deletions/duplications by low coverage massively parallel sequencing," Prenatal Diagnosis, 2013, pp. 584-590, vol. 33.

Fan, H.C., et al., "Sensitivity of Noninvasive Prenatal Detection of Fetal Aneuploidy from Maternal Plasma Using Shotgun Sequencing Is Limited Only by Counting Statistics," PLoS ONE, 2010, pp. 1-7, vol. 5, Issue 5, e10439.

Lo, K. K., et al., "Limited Clinical Utility of Non-invasive Prenatal Testing for Subchromosomal Abnormalities," The American Journal of Human Genetics, 2016, pp. 34-44, vol. 98.

Ross, M. G., et al., "Characterizing and measuring bias in sequence data," Genome Biology, 2013, pp. 1-20, vol. 14, No. R51.

Sehnert, A. J., et al., "Optimal Detection of Fetal Chromosomal Abnormalities by Massively Parallel DNA Sequencing of Cell-Free Fetal DNA from Maternal Blood," Clinical Chemistry, 2011, pp. 1042-1049, vol. 57, Issue 7.

Yu, S.C.Y., et al., "Noninvasive Prenatal Molecular Karyotyping from Maternal Plasma," PLoS ONE, 2013, pp. 1-8, vol. 8, Issue 4, e60968.

Yua, S. C. Y., et al., "Size-based molecular diagnostics using plasma DNA for noninvasive prenatal testing," PNAS, Jun. 10, 2014, pp. 8583-8588, vol. 111, No. 23.

Zhao, C., et al., "Detection of Fetal Subchromosomal Abnormalities by Sequencing Circulating Cell-Free DNA from Maternal Plasma," Clinical Chemistry, 2015, pp. 608-616 vol. 61, Issue 4.

* cited by examiner

*Primary Examiner* — John S Brusca
(74) *Attorney, Agent, or Firm* — Wolter VanDyke Davis, PLLC; Eugene J. Molinelli

(57) ABSTRACT

Techniques for automated determination or correction of count bias are based on nucleic acid base content on a finer grained scale than a bin of interest in a target sequence. The techniques include obtaining a target sequence with bins where relative abundances indicate a condition and raw counts $H_j$ of reads, from a subject, which start at each locus j. A partition indicates a fine-grained window at a position relative to a current locus and multiple strata indicating different base contents. Each locus is attributed to one stratum k(j). An expected count of each stratum, E(k), is determined based on $H_j$ for j belonging to the stratum and a number of loci in the target belonging to the stratum. A copy number of a bin is based on a sum of E(k(j)) in the bin. Output data indicates condition of the subject based at least partly on the copy number.

15 Claims, 15 Drawing Sheets

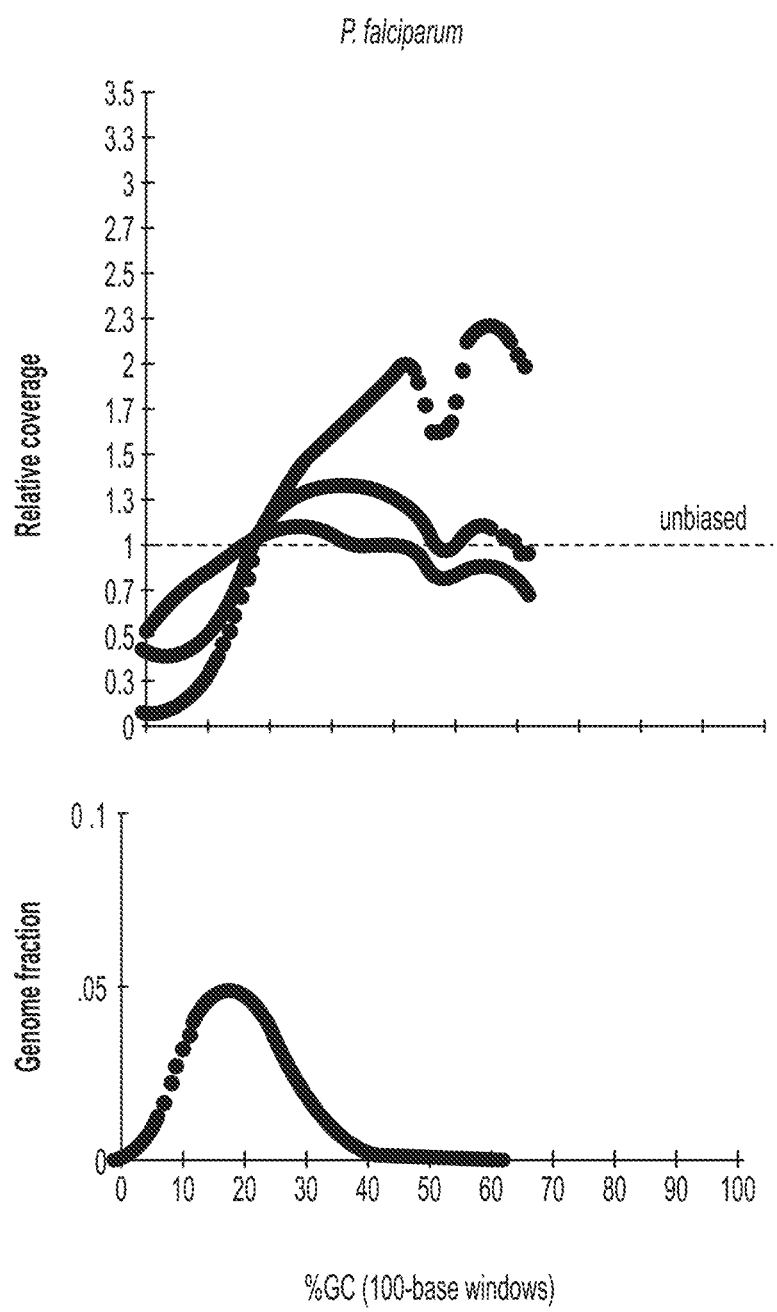

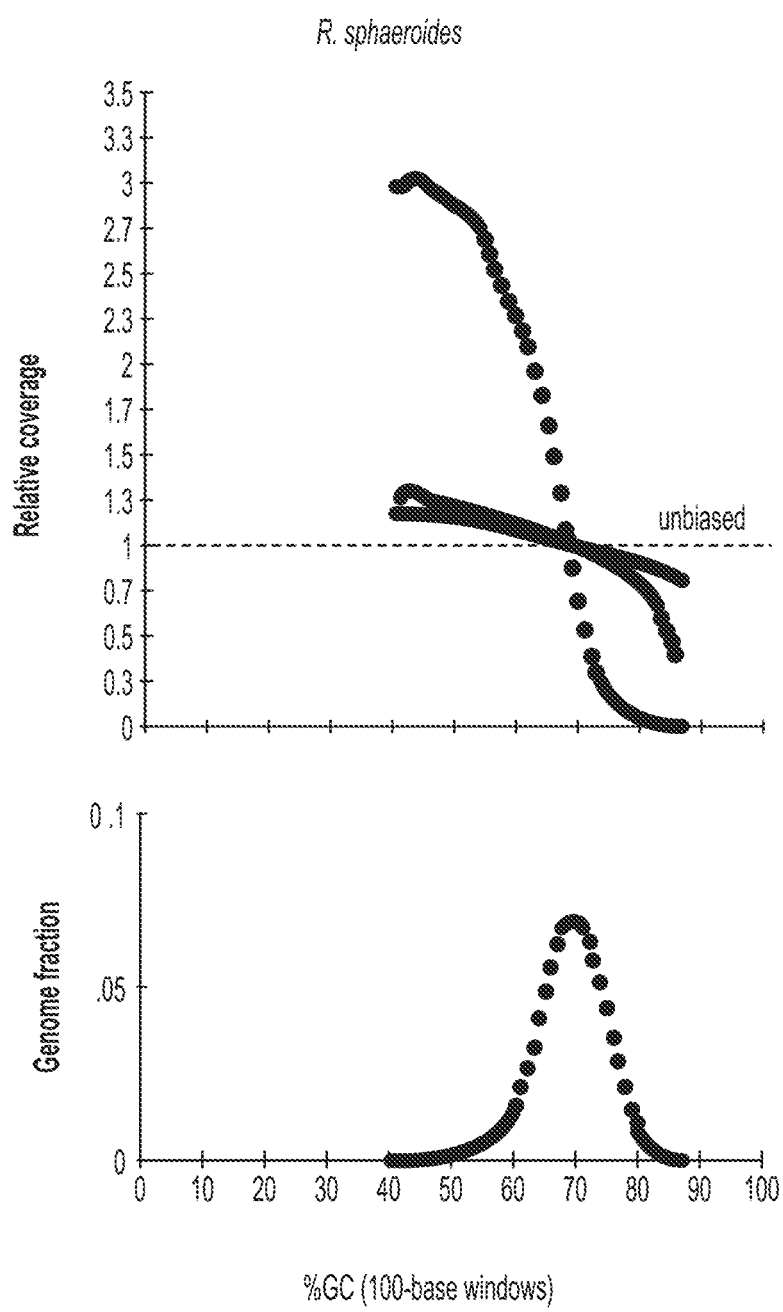

TECHNIQUES FOR FINE GRAINED CORRECTION OF COUNT BIAS IN MASSIVELY PARALLEL DNA SEQUENCING

CROSS-REFERENCE TO RELATED APPLICATIONS

This application claims benefit of Provisional Appln. 62/400,610, filed Sep. 27, 2016, the entire contents of which are hereby incorporated by reference as if fully set forth herein, under 35 U.S.C. § 119.

BACKGROUND

Massively Parallel Sequencing (MPS) approaches such as those now in wide commercial use (Illumina/Solexa, Roche/454 Pyrosequencing, and ABI SOLiD) are attractive tools for sequencing. Typically, MPS methods can only obtain short read lengths (hundreds of base pairs, bp, also called nucleotides, nt, with Illumina platforms, to a maximum of 200-300 nt by 454 Pyrosequencing) but perform many thousands to millions of such short reads on the order of hours. Sanger methods, on the other hand, achieve longer read lengths of approximately 800 nt (typically 500-600 nt with non-enriched DNA) but take several times longer to do so.

While sequencing machines were originally created for the purposes of sequencing unknown or incomplete genomic DNA, they have since been put to a myriad of other uses. Considering a sequencer simply as a device for recording the count of specific DNA sequences, sequence census experiments utilize high-throughput sequencing to estimate abundances of "target sequences" (also called "reference sequences") for molecular biology and biomedical applications. Unusual populations of certain reference sequences can be diagnostic of disease.

To compare the DNA of the sequenced sample to its reference sequence, current methods are designed to find the corresponding part of that sequence for each read in the output sequencing data. This step is called aligning or mapping the reads against the reference sequence. Once this is done, one can look for one or more variations (e.g., a single nucleotide polymorphism, SNP, or a copy number variation, CNV, or a structural variation like presence/absence variation, PAV, or multiples or combinations thereof) within the sample. Aligning the read to the reference consumes a considerable amount of computing power.

For example, Sehnert et al 2011 and Biananchi et al 2014 describe methods to identify aneuploidy in a fetus from maternal blood samples, thus avoiding expensive and dangerous invasive procedures. Aneuploidy is a condition in which the number of chromosomes in the nucleus of a cell abnormal for a particular species. In humans, the normal cell has two copies of each chromosome, called diploid, while an aberrant cell might have fewer copies (0 called a deletion, 1 called monosomy) or more copies (3 called trisomy, etc.). An extra or missing chromosome, or a significant portion thereof, is called a copy number variation (CNV), and is a common cause of genetic disorders including human birth defects. The fetal DNA in maternal blood is a very small fraction of the sample (e.g., less than 10% and often as little as 0.5%) and the identification of its sequences is thus subject to systematic and random errors in the sample preparation, sequencing and alignment processes. Detecting fetal anomalies in the mother's blood is a form of non-invasive pre-natal diagnostics (NIPD).

Similarly, cancerous tumors may have copy number variations (CNVs), presence absence variations (PAVs), other structural mutations, or express different genes than the populations of normal cells in an individual. The tumor DNA in a patient tissue sample is likewise a relatively small fraction of the sample (e.g., less than 15% and sometimes as little as 0.5%) and the identification of its sequences is likewise subject to systematic bias and random errors in the sample preparation, sequencing and alignment processes.

Thus, errors and bias in read number and alignment from modern sequencing technology and data processing can obfuscate the underlying biological relationships desired to be discovered to diagnose or track various medical conditions. A bias in the count of reads associated with a particular stretch of a target sequence is called a count bias.

SUMMARY

Techniques are provided for automated determination of, or correction for, count bias, or both, based on nucleic acid base content on a finer grained scale than a bin of interest in a target sequence.

In a first set of embodiments, a method executed on a processor includes obtaining first data that indicates a target sequence of nucleic acid bases at a plurality of loci. The target sequence includes multiple bins of loci for which a relative abundance is indicative of a condition of interest. The method also includes obtaining second data that indicates alignment with the target sequence of reads of DNA fragments in a sample from a subject; and, determining a raw count Hj of reads that start at each locus j. Furthermore, the method includes obtaining partition data that indicates, for a first partition, a window that includes a number of bases less than a number of bases in a bin and that has a position relative to a current locus (e.g., centered on or starting at the current locus). The partition data for the first partition also indicates multiple strata based on corresponding different contents of nucleic acid bases in the window (e.g., percent GC content). The method still further includes attributing to each locus j in the target sequence a stratum k(j) of the multiple strata of the first partition based on the content of nucleic acid bases in the target sequence in the window relative to the locus j. The method even further includes determining an expected count of each stratum, E(k), in the first partition based on the raw counts Hj of each locus j belonging to the stratum k and a total number of loci in the target sequence belonging to the stratum k. Yet even further, the method includes determining a copy number of a first bin based on a sum over all loci in the first bin of E(k(j)) for the first partition. And even still further, the method includes presenting on a display, output data that indicates condition of the subject based at least in part on the copy number of the first bin.

In some embodiments of the first set, the method still further includes determining a copy number of a second bin based on a sum over all loci in the second bin of E(k(j)) for the first partition. In these embodiments, the condition of the subject is based also at least in part on the copy number of the second bin.

In some embodiments of the first set, the method still further includes repeating steps that involve the first partition for a second partition different from the first partition. In these embodiments, determining the copy number of the first bin includes determining the copy number of the first bin based on the sum over all loci in the first bin of E(k(j)) for the first partition weighted by a probability of the first partition and a sum over all loci in the first bin of E(k(j)) for the second partition weighted by a probability of the second partition.

In other sets of embodiments, a computer-readable medium or a system is configured to cause an apparatus to perform one or more steps of one or more of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 3A through FIG. 3C are graph pairs that illustrate example relative count bias associated with percent GC content, which bias is to be corrected, according to an embodiment;

DETAILED DESCRIPTION

Figure 1A:
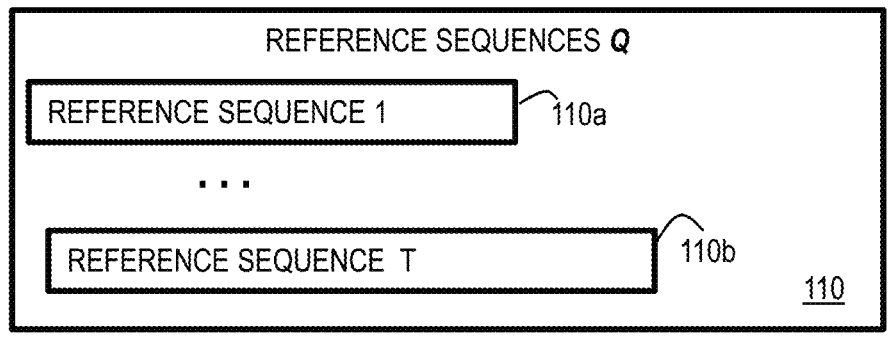
FIG. 1A through FIG. 1C are block diagrams that illustrate relative abundance of reference sequences in a sample.

A method and apparatus are described for fine grained detection or correction of count bias. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader rang around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of count bias based on GC percent in overlapping windows of size from about 100 bases to about 160 bases at a resolution of a single base. However, the invention is not limited to this context. In other embodiments other sizes of other overlapping or non-overlapping windows placed relative to an individual locus are determined based on other properties of the base content in the window, such as AT repeats in the window, or some combination.

1. OVERVIEW

Deoxyribonucleic acid (DNA) is a, usually double-stranded, long molecule that is used by biological cells to encode other shorter molecules, such as proteins, used to build and control all living organisms. DNA is composed of repeating chemical units known as "nucleotides" or "bases." There are four bases: adenine, thymine, cytosine, and guanine, represented by the letters A, T, C and G, respectively. Adenine on one strand of DNA always binds to thymine on the other strand of DNA; and guanine on one strand always binds to cytosine on the other strand and such bonds are called base pairs. Any order of A, T, C and G is allowed on one strand, and that order determines the reverse complementary order on the other strand. The actual order determines the function of that portion of the DNA molecule. Information on a portion of one strand of DNA can be captured by ribonucleic acid (RNA) that also is composed of a chain of nucleotides in which uracil (U) replaces thymine (T). Determining the order, or sequence, of bases on one strand of DNA or RNA is called sequencing. A portion of length k bases of a strand is called a k-mer; and specific short k-mers are called oligonucleotides or oligomers or "oligos" for short.

Figure 1B:
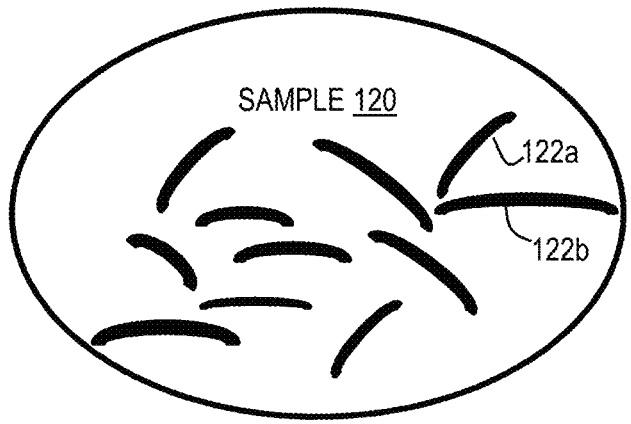
Figure 1C:
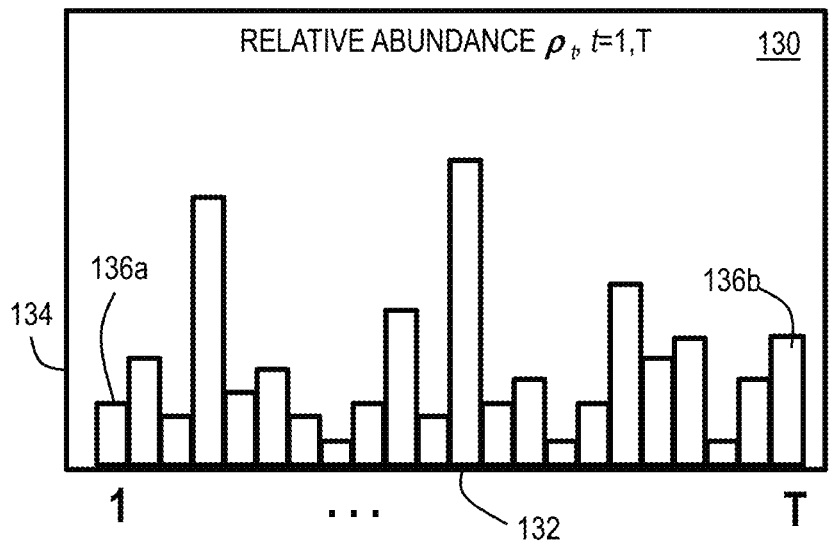

FIG. 1A through FIG. 1C are block diagrams that illustrate relative abundance of reference sequences in a sample. FIG. 1A is a block diagram that illustrates an example data structure 110 of T reference sequences Q, including field 110a holding data that indicates first reference sequence ($Q_1$), through field 110b holding the last (Tth) reference sequence ($Q_T$), among others indicated by ellipsis. An individual reference sequence is indicated by Qt, where t∈{1, . . . , T}. A reference sequence can refer to a normal (also called most common or consensus sequence or baseline or disease free sequence) or a SNP, CNV, PAV or other known structural variation of the normal sequence. The reference sequence can be an entire genome of a subject or population of subjects, or one or more chromosomes of the genome, or one or more regions of interest, such as sequences of a fixed size on one or more chromosomes, including all contiguous bases or excluding one or more bases at particular locations, as specified by a mask of locations of no interest. The term bin will refer to each of one or more such regions of interest, in some embodiments excluding bases specified in such a mask, if any.

FIG. 1B is a block diagram that represents an example sample 120 with multiple occurrences of nucleic acids, e.g., 122a, 122b (collectively referenced hereinafter as nucleic acids 122) each having at least one of the reference sequences or a fragment thereof (e.g., in the case of extracellular DNA in the blood of a subject from tumors or fetal cells). There may be several occurrences of a nucleic acid with one of the reference sequences and few or no occurrences of nucleic acids with another of the reference sequences. FIG. 1C is a bar graph 130 that illustrates example relative abundance data. The horizontal axis 132 indicates the reference sequences $Q_t$ {t=1, T}. The vertical axis 134 indicates relative number of nucleic acids in the sample (designated by the symbol ρ) with each reference, with a higher value indicating a greater abundance of the associated reference sequence. Graph 130 indicates that $Q_1$ occurs in the sample 120 with a relative abundance $\rho_1$ indicated by bar 136a, and $Q_T$ occurs in the sample 120 with a relative abundance $\rho_{TT}$ indicated by bar 136b. The abundance distribution is represented by ρ=$\rho_t$, {t=1,T}.

A problem is that ρ is not measured directly during sequencing experiments, but must be inferred by a large number S of sequencing reads (simply called reads, herein), represented by the symbol $q_s$ {s=1, S}, where each sequence of each read is short compared to a reference sequence $Q_t$.

Figure 1D:
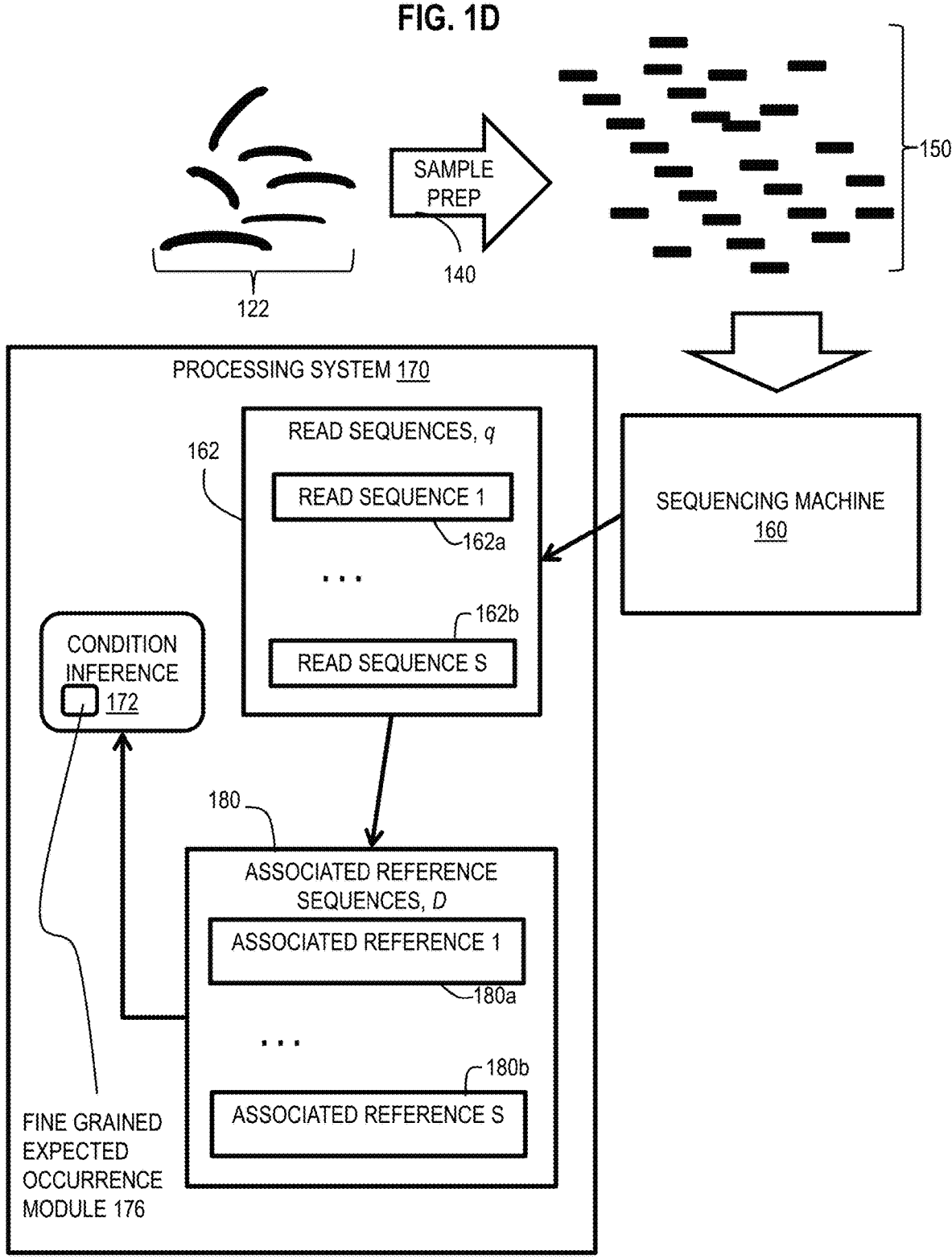
FIG. 1D is a block diagram that illustrates an example process to obtain reads from a sample and associate reads with reference sequences, according to an embodiment.

FIG. 1D is a block diagram that illustrates an example process to obtain reads from a sample and associate reads with reference sequences, according to an embodiment. The nucleic acids 122 in a sample are prepared for the sequencer in a wide variety of ways known in the art, often by de-naturing to release the nucleic acids, fragmentation to allow the short reads to begin sequencing from anywhere within the nucleic acid having the reference sequence, to hybridization or replication or amplification or size selection, among others, or some combination, which collectively are referenced herein as sample preparation process 140. The resulting short nucleic acids 150 are then sequenced with whatever bias or systematic variation are introduced by the sequencing process in sequencing machine 160. The reads $q_s$ {s=1, S} are recorded in a data structure 162 with a field holding data that represents each read sequence, such as field 162a for $q_1$ to field 162b for $q_S$, among others indicated by ellipsis.

If each read were uniquely found in one and only one reference sequence, then one of the T reference sequences $Q_t$ can be associated with each read, as indicated by the data structure 180 which associates with each read $q_s$ {s∈1, S} an associated reference sequence $D_s$, with s∈{1, . . . , S} and where $D_s$=t with t∈{1, . . . , T}. In some embodiments, the data structure 180 also indicates the positions within the reference sequence t that are covered by the read, such as positions x to y within the reference sequence t. If a read could be associated with two or more difference reference sequences, then the read is attributed to one of them, or a fraction of the read is attributed to each of two or more of them, or the read is discarded. Then a histogram of the distribution of the $D_s$ among the T references sequences could be used as an approximation of the abundance distribution ρ, or corrected for the known or inferred non-random sampling introduced by processes 140 and machine 160—corrections represented by particular values for a parameters set designated θ. The adjusted abundances are designated $A_t$ and are based on the histogram counts for the associated reference sequences $D_s$ and the corrections represented by values for θ.

In FIG. 1D, the read sequences data structure 162 and associated reference sequences data structure 180 reside on a processing system 170, such as computer system described below with reference to FIG. 6 or one or more chip sets as described below with reference to FIG. 7, or some combination. The associated reference sequences $D_s$ are converted to adjusted abundances $A_t$ and used to infer a condition of a subject that contributed the sample 120 by condition inference module 172 implemented within the processing system 170. Although processes, equipment, and data structures are depicted in FIG. 1A through FIG. 1D as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, in various embodiments, one or both of the data structures 162, 180 or all or part of module 172, or some combination, reside within one or more chip sets in the sequencing machine 160.

Thus the clinical data comprises the adjusted counts $A_t$ {t=1, T) of the T reference sequences Q after correction for known systematic errors introduced by the processes 140 and machine 160. Based on the analysis of historical data or other training data, with either baseline (disease free) or known diseased conditions or known other conditions of interest, or some combination, the presence of a disease or other population differences is known to affect the count of at least one of the reference sequences, t=i but not, or much less, the counts of the other reference sequences t=k≠i. However, variation between runs or processing batches, which has nothing to do with disease state, can confound identification of disease by affecting the count $A_i$.

Because the fetal or tumor fraction is so small, other confounding factors that affect the measured counts of the target are advantageously removed to form adjusted counts $A_i$ or $A_j$. Several such adjustments are known in the art. Analysis is further complicated because, in order to be economically viable, samples are run in multiplex which reduces the read coverage of each sample. In the multiplexed sequencing method, DNA libraries are "tagged" with a unique identifier, or index, during sample preparation. Multiple samples are then pooled into a single lane on a flow cell and sequenced together in one Genome Analyzer run. An automated three-read sequencing strategy identifies each uniquely tagged sample for individual downstream analysis. Using this approach, sample identification is highly accurate. However, reducing read coverage results in less accurate identification of CNVs (Zhou et al 2015), which is of importance in several embodiments describe herein.

Known systems (such as those described by Lo et al 2016; Yuy et al 2013; Chen et al 2013; Zhou et al 2015; Sehnert et al 2011; Fan and Quake 2010; and inventor's own work published as international patent application publication WO 2017/079398 and as US patent publications US 2016/0335392, divide the chromosome into bins of 20-100 kilobases. Use of bins accomplishes two things: first, division into bins allows nuisance loci (such as copy number variations in the mother, and centromeres) to be easily dropped from the estimated chromosome or region of interest (ROI) scores; second, making bins of sufficient size allows a bin center (such as mean normalized coverage) called the "bin effect," to be accurately estimated under normal conditions (null hypothesis), and corrected for. The known systems are then corrected for known effects (such as the proportion of "G" or "C" bases in the bin, called GC effect, and other locus effects) to form adjusted counts $A_i$ called "bin scores" before combining bin scores to form chromosome or ROI level scores which are transformed into a Z-score or otherwise evaluated for significant deviation from null (normal) behavior. Some of the known methods also model noise in normal cases via principal components or singular value decomposition of bin covariance or correlation and removing a "noise effect". One limitation of the above methods is that estimation of effects for GC and other factors require large sets of normal samples. This can be expensive and presents a "cold start" barrier condition for smaller laboratories hoping to start NIPD programs. A second limitation of the above methods is that correction of confounding effects at the bin level still leaves enough bin-to-bin variability to decreases accuracy of multiplex samples at smaller fetal fractions.

As described here, additional adjustments are made to reduce the effects of count bias, which is often about an order of magnitude larger than the condition of interest, especially for fetal or tumor or other small fraction signals. The approach presented here provides a fine grained correction (small numbers of bases compared to bin size) for count bias based on locus associated with each fragment or read, rather than on the position and bases of the entire bin. In embodiments using extra-cellular DNA fragments, the system also corrects for the bias in the natural formation of such fragments, e.g. from the tumor or fetal DNA, before or after introduction into the bloodstream of the subject. In the system of FIG. 1D, the new approach is implemented as a fine-grained expected occurrence module 176 in the condition inference module 172.

Figure 2:
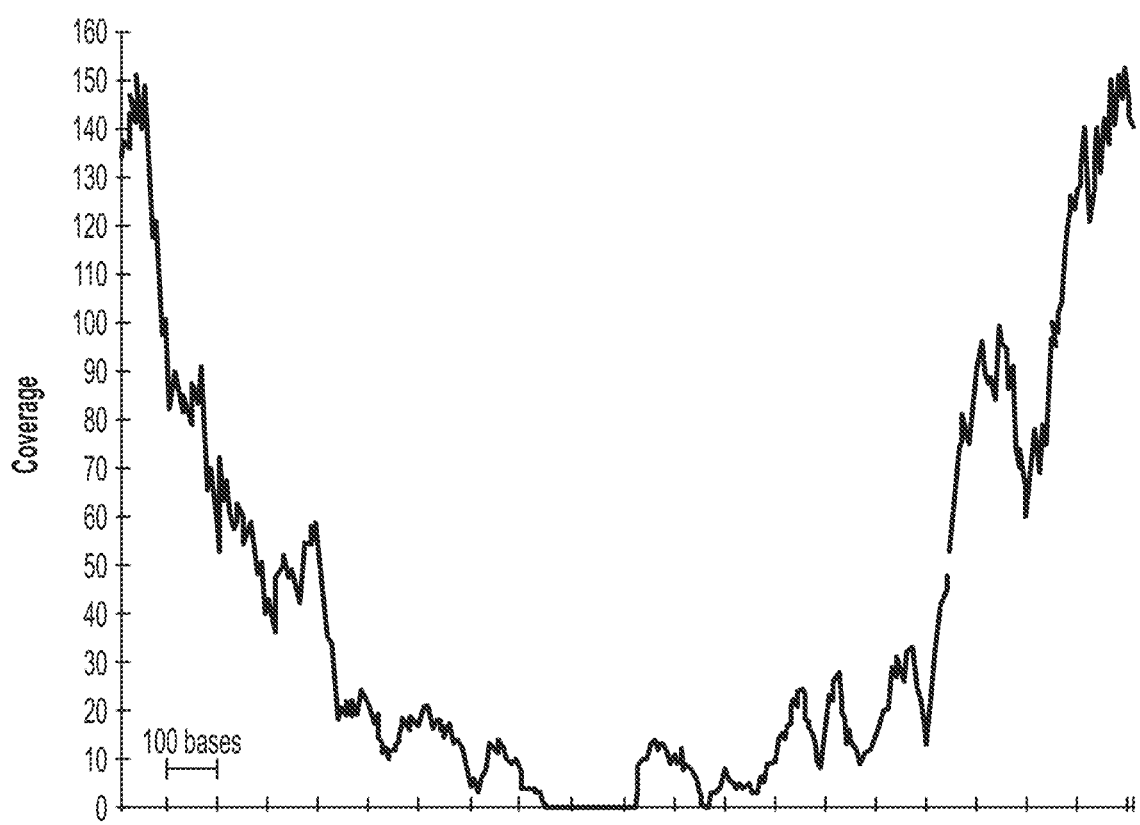
FIG. 2 is a graph that illustrates example coverage variations along a reference sequence to be corrected, according to an embodiment.

As an example of count bias, consider the data presented in Ross, 2012. FIG. 2 is a graph that illustrates example coverage variations along a reference sequence to be corrected, according to an embodiment. The horizontal axis indicates each base position in a 2000 base portion of the genome, and the vertical axis indicates the number of times the locus is covered by one of the reads. Sufficient reads were collected to cover every base location 198 times, called a 198× whole-genome shotgun data set. As depicted in the graph, over 100 bases of this 2,000 base region were uncovered, very few of the base locations were covered by even half of the 192×, while the coverage of other basses varied by two orders of magnitude. Relative abundance of regions of interest would have to be averaged over many kilobase positions to hope to average out this kind of variability. Thus bins are often defined with sizes on the order of many kilobases.

Figure 3B:
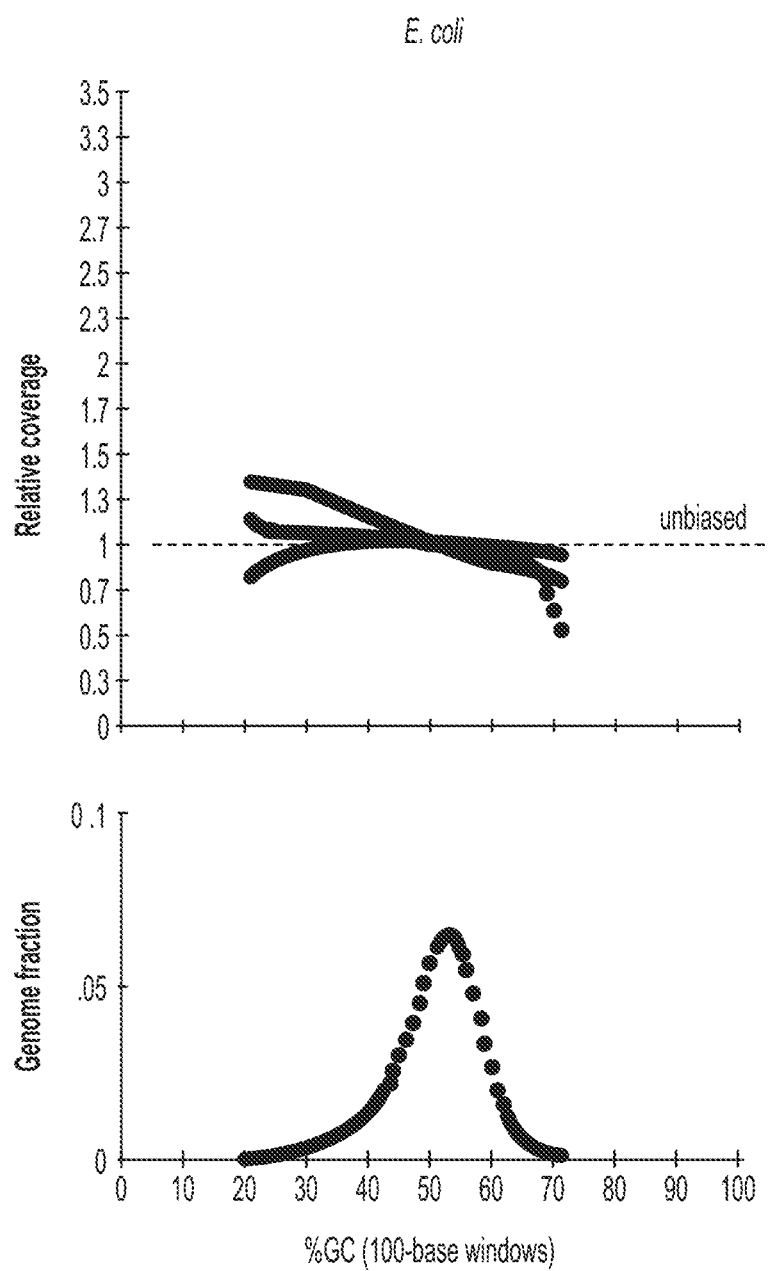

However, the kind of variability depicted in FIG. 2 is not completely random. Much of the variability is explained by the base content of the uncovered and under-covered sections. It is known that percent of G and C bases is related to the under-coverage; for example, under-coverage of loci windows including a low GC content (less than 25% of locus positions in windows of 100 locus positions) or high CG content (over 75% of locus positions in windows of 100 locus positions). FIG. 3A through FIG. 3C are graph pairs that illustrate example relative count bias associated with percent GC content, which bias is to be automatically discovered or corrected or both, according to an embodiment. These data are presented by Ross, 2012. Each of FIG. 3A through FIG. 3C depicts, in the lower graph of the pair, the genome fraction with a certain GC content in a 100 base window and depicts in the upper graph of the pair the relative coverage of those windows using conventional read and alignment processing. The horizontal axis on all plots indicates the percent of the 100 loci that are populated by either G or C bases, called % GC content. The vertical axis of the lower graph indicates a fraction of the genome with such content in a 100 base window. The vertical axis on the upper graph indicates the relative coverage, that is the fraction observed divided by the fraction in the genome (from the lower figure). A value of 1 indicates the relative coverage is correct, that the coverage is "un-biased."

FIG. 3A depicts a genome of a species, *P. falciparum,* with many 100-base windows having GC content less than about 20%. These low GC content windows are under-covered, having relative coverage less than 1 and coverage proportional to, and increasing with, the % GC content. FIG. 3B depicts a genome of a species, *E. coli,* with most 100-base windows having medium GC content between about 20% and about 70%. These middle GC content windows are comparatively un-biased, having relative coverage of about 1 and nearly independent of the % GC content. FIG. 3C depicts a genome of a species, *R. sphaeroides,* with many 100-base windows having GC content greater than about 70%. These high GC content windows are also under-covered, having relative coverage less than 1 and coverage proportional to, and decreasing with, the % GC content. A method to automatically determine and correct for such count bias is useful.

Figure 4:
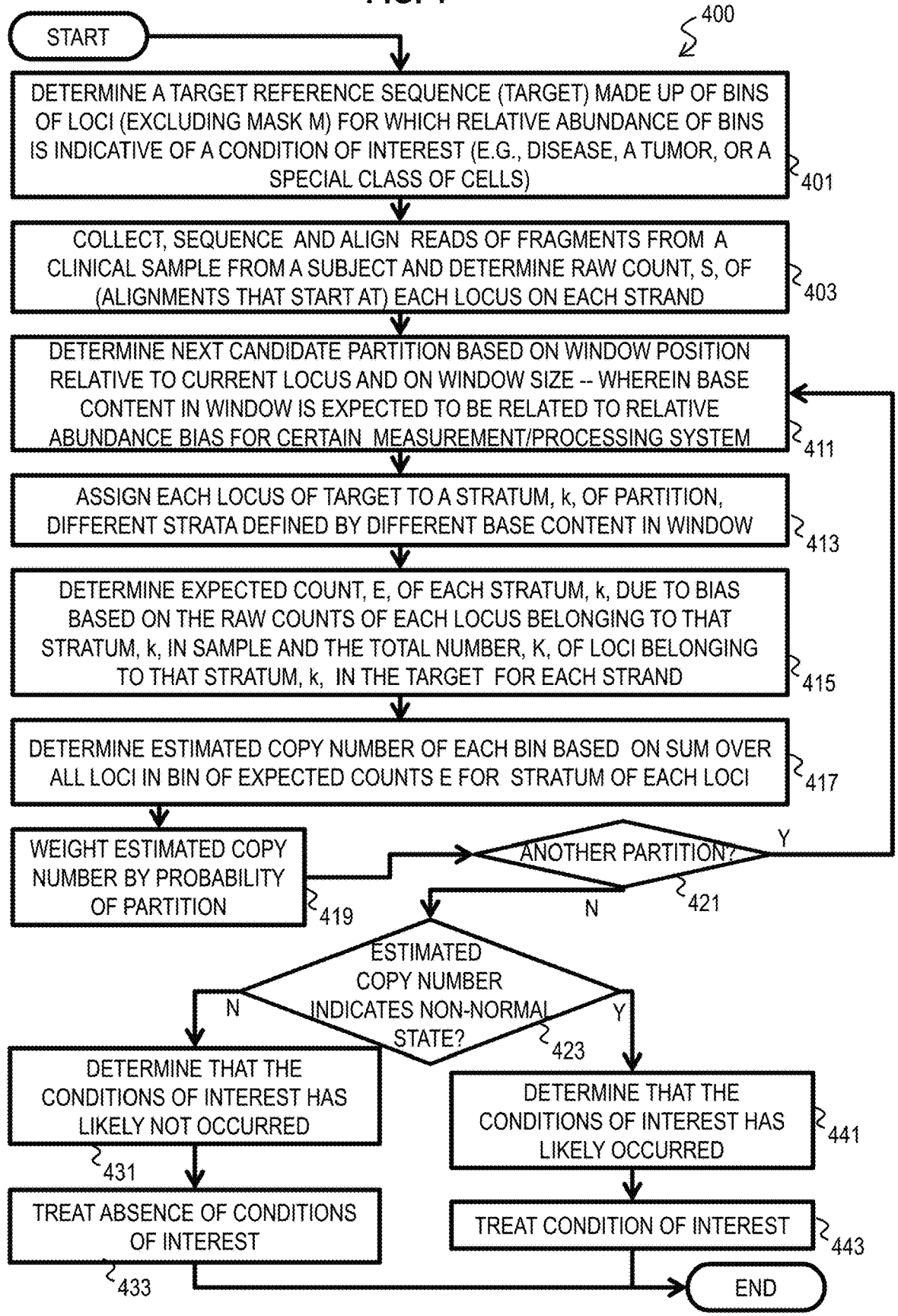
FIG. 4 is a flow chart that illustrates an example method to estimate and correct for count bias based on content at each locus of interest, according to an embodiment.

FIG. 4 is a flow chart that illustrates an example method 400 to estimate and correct for count bias based on content at each locus of interest, according to an embodiment. The method 400 can be used to discover or utilize any content based count bias on any scale, including very fine scale and locus specific biases, not just the 100 locus windows of % GC content depicted in FIG. 3A through FIG. 3B or the bin-scale biases determined using other previous approaches. For example, the bias could be discovered and corrected due to repeats of individual bases or base pairs, such as AT base pair repeats, or other patterns of base content, and even combinations of several different content-based bias effects. Thus the method corrects for base content effects at the individual base level. The method can be run at the individual sample level so that large numbers of samples are not needed to apply the method. The method corrects for biases even if the bias is invisible at the bin level. The method can be used by itself to detect low fetal fraction CNVs or as a pre-processing variance reduction step for existing bin level CNV NIPD systems. Although steps are depicted in FIG. 4 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In this description, the following terms and definitions are employed. |X| is the cardinality of a set X. |X| is equal to the number of elements in the set X. The cardinality of a set is also called the size of the set. When F is a function and X is a set, |F(X)| is the number of unique values that F can attain when applied to members of the set X. X\Y is the set of elements that remain when members of set X that are also members of set Y are removed and the operation is referred to as set subtraction. The expression pr(a|b) indicates the probability of condition a, given condition b. The expression E(a|b) indicates the expected value of variable a, given condition b. A partition P of a set X is a grouping into subsets so that each element of X is in one and only one subset. The partition P is essentially a function of X, and has cardinality |P|. The subsets used to define a partition P are called partition subsets; and, each partition subset of P is designated by the index k, k∈{1, . . . , |P|}. Stratification of a set X means defining a partition and assigning each element of set X into a partition subset. The stratum of an element of the set X is the partition subset to which the element belongs.

The method 400 partitions the genome of a species into non-contiguous subsets based on nucleotide (base) content in small windows relative to each position in the genome, because count bias at each position is expected to be related to base content in the vicinity of that position. The method allows the base content and the vicinity to be varied to discover or correct for, or both, one or more count biases affected by base content. The window size is small compared to the bin sizes and the resolution of the method can be finer than even the window size, as fine as each locus, by using overlapping windows.

With respect to partitioning the genome of a species, the following terms and definitions are employed. Base positions in the genome are called "positions" or "loci" and are indexed by the variable j where j∈{1, . . . , N}, where N is the number of loci in the genome of the species. In humans N is about three billion. To simplify the computations, it is often advantageous to exclude loci of no interest or confounding effect. This is done with a mask M. M is a mask of genomic positions that are excluded from all analysis and may be considered to be applied at the level of defining the target sequence. M may be considered an array or a set depending on context. Masks are often designed to cover features, such as centromeres, that confound analysis because their composition diverges greatly from the rest of the genome. M is indexed by locus position j; when M(j)=0 the position j is removed or excluded from analysis; otherwise M(j)=1.

The Partition P is based on the nucleotide content in a window R of a given size; and, if several partitioning schemes are under consideration, the different partitions are designated by different values of the index i, i∈{1, . . . , I}, where I indicates the number of partitioning schemes. Given a genomic locus, j, par_i(j) is the index of the strata (partition element, k) of a single partition Pi to which position j belongs, par_i(j)∈{1, . . . , |Pi|}. When a single partitioning scheme is considered, the symbols are simplified to partition P and stratum par(j).

In step 401, a target sequence (target) is determined. The target includes one or more reference sequences, t, called bins, each bin covering a range of loci but, in some embodiments, excluding loci in a mask M. The number of bins is indicated by T, e.g., in data structure 110. The bins are selected because relative abundance of bins is indicative of a condition of interest (e.g., disease, a tumor, or a special class of cells). Each bin may encompass one or more chromosomes of a species, or portions thereof. Bin sizes are large, on the order of thousands to millions of loci. Any method may be used to determine the target, including obtaining the target from known sources, or receiving manual input of bin loci ranges or masks or both, or automatically retrieving such sequences, ranges or masks or all from storage, or receiving such sequences or ranges or masks or all from a remote computer across a network, either unsolicited or in response to a query.

Figure 5:
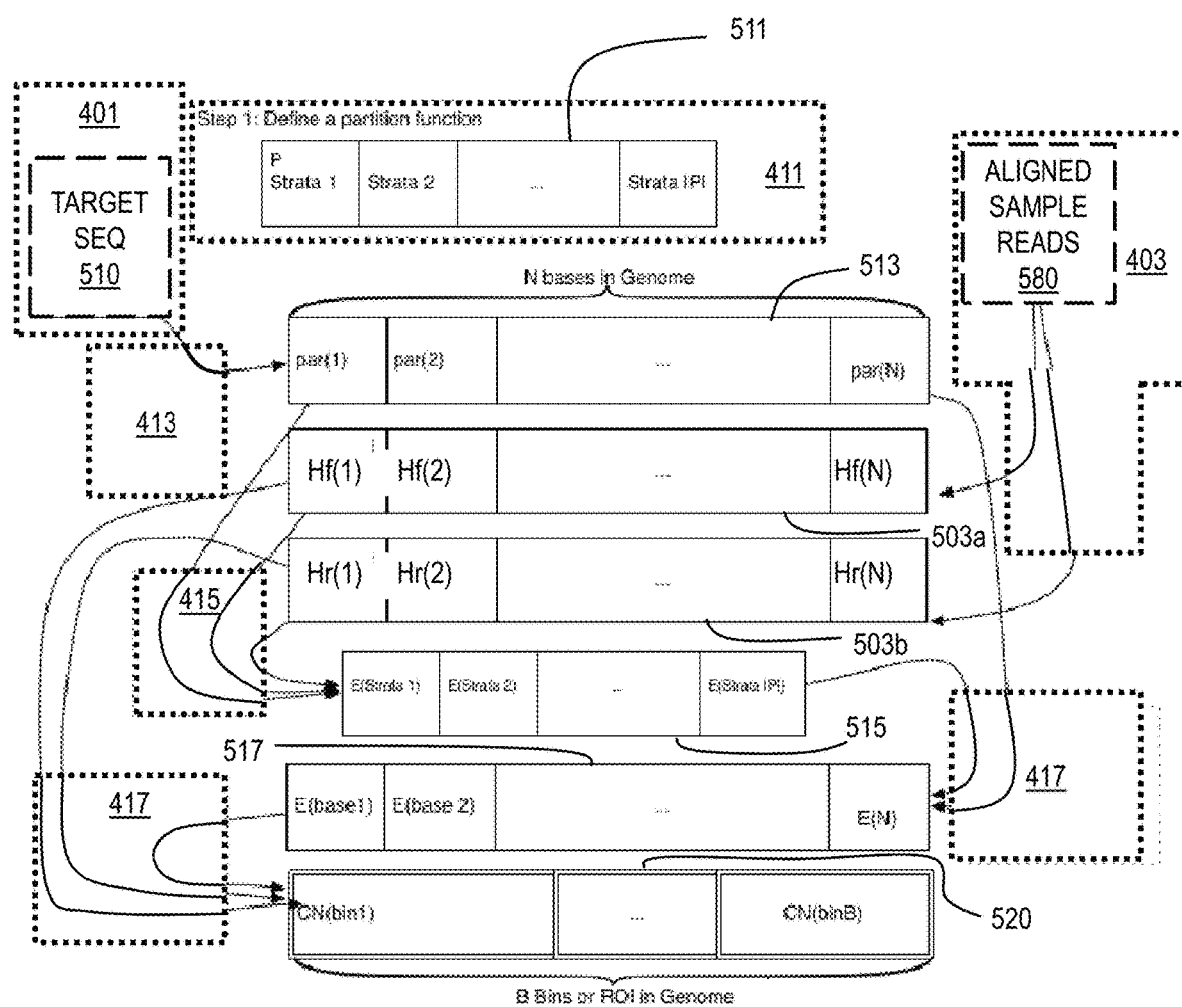
FIG. 5 is a block diagram that illustrates example data structures produced after each of several steps described in FIG. 4, according to an embodiment.

FIG. 5 is a block diagram that illustrates example data structures produced during each of several steps described in FIG. 4, according to an embodiment. In FIG. 5, the input reference genome (target) data 510 is provided during step 401. In some embodiments, the target 510 is stored, locally or remotely, as described by data structure 110 in FIG. 1A.

Returning to FIG. 4, in step 403, reads of fragments in a clinical sample from a subject are collected, sequenced and aligned and a raw count of alignments that start at each locus, or at some fixed offset from each locus, on each strand are determined. Any method may be used that provides a sample that has been sequenced and aligned to a reference genome.

In some embodiments, given a large number of samples, an automated process iterates through the alignments and catalogs which positions are never covered. The positions never covered are added to the mask, M.

If there are S total reads, then there are S loci associated with the start of each aligned read; and, if the reads average L bases in length, then there are L*S bases covered. The number of reads that start at each locus j, or at some fixed offset from each locus j, is designated H(j). Note that there are forward and reverse start locations, corresponding to a forward strand and a reverse (complementary) strand. Hforward, Hf, is an array of numbers, one per locus of the forward strand. Hf(j) is the number of alignments from the sample which start at base j (or start as some fixed offset from j) on the forward strand. If strand specific partition levels are defined then Hreverse, Hr, is defined as the number of alignments from the sample which start at base j on the reverse (complementary) strand. When only one strand is read, the symbols are simplified to H(j).

In FIG. 5, the input aligned sample reads data 580 is provided during step 403. In some embodiments, the aligned sample reads data 580 is provided as described by data structure 180 in FIG. 1D, each associated reference data element 180 indicating a start locus and direction or loci range associated with each read. The number of reads that start at each locus are determined in step 403 and stored in the array H(j), or Hforward(j) and Hreverse(j). FIG. 5 depicts the two arrays Hforward and Hreverse as data structures 503a and 503b, respectively. FIG. 5 also depicts data fields in each data structure for locus (base position) 1 through locus N, and labels individual fields by the abbreviations Hf(1), Hf(2) and Hf(N) for the array members of Hforward, and by the abbreviations Hr(1), Hr(2) and Hr(N) for the array members of Hreverse. These data structures may be in either fast volatile memory or in permanent memory of some sort, or some combination, as described in the section below on computational hardware.

Returning to FIG. 4, in step 411, the next Pi of one or more partitions is defined. A partition definition is data that indicates a window size and the window location relative to an arbitrary locus in the target sequence, and multiple strata for the locus based on nucleotide base content in the window. The set of nucleotide bases in a window is indicated by the symbol R. For example, in various embodiments, a partition based on the data of FIG. 3A through FIG. 3C could be defined by a window R of size 100 loci, either centered on or starting at the locus to which the partition is applied. The strata could be defined by 5% steps in percent GC content in the window R. Different count biases are expected in different strata. Thus step 411 determines next candidate partition based on window position relative to current locus and on window size—wherein base content in the window R is expected to be related to relative abundance bias at the locus for a certain measurement/processing system. In some embodiments, partitions are known but quantitative effects of the partitions are not known. In some embodiments, a favorable partition is not known, so an arbitrary partition or a random partition or a suggested partition is tried and, based on the results as described below, the partition is adopted or given a high or low probability.

In FIG. 5, step 411 is depicted as producing data structure 511 for a partition, which is a function of the set of target sequence loci. Based on the nucleotide base content in the vicinity of the locus, the locus is assigned to one of the strata. In some embodiments, the partition is a data structure holding the window size and relative location compared to the locus, an expression that indicates the function of the nucleotide content in the window, and a table that lists function value ranges that belong to, or threshold values that separate, each of |P| different strata. In some embodiments, the partition definition is a data structure that holds just the window definition and a functional form, e.g., an integer function of a property of the nucleotide base content in the window, such as the integer floor of the % GC content or the number of contiguous repeats of an AT nucleotide base sequence. The integer floor of an argument is the largest integer less than or equal to the argument. The integer output of an integer function indicates the stratum k (e.g., par_i(j)) for the locus j in that particular partition Pi.

Returning to FIG. 4, in step 413, each locus of the target sequence is assigned to a stratum, k, of partition Pi. In FIG. 5, this is depicted for a single partition, P, by the value of par(j) for the loci j from 1 through N in data structure 513. Three fields in the data structure 513 are labeled by the elements of the array par(j) corresponding to those fields, including the first two fields, par(1) and par(2) and the last field, par(N). By doing so, each count in the arrays 503a and 503b is also associated with a stratum of the partition P; because each count Hf(j) and Hr(j) is associated with locus j which by data structure 513 is associated with par(j).

Returning to FIG. 4, in step 415, the deviation in count due to bias, (also called expected count hereinafter) is determined for each stratum, k, of partition Pi. The count for each stratum, if every locus were equally represented at the start of a read, would be proportional to the number of loci j that belong to each stratum k. Letting K represent the set of forward genomic positions where par(j)=k, the number of loci j that belong to the stratum k is represented by the symbol |K|. If the mask is not necessarily applied at the definition of the target sequence, then it can be applied here and represented by the symbol |K\M|. However, due to count bias in a particular measurement and processing system, the occurrence of counts in the sample for different strata do not follow the value of |K\M| for different strata. This deviation affects the expected counts for each stratum for that particular measurement system for the species. The actual counts observed in the sample depend on the bias and are obtained by summing all values of H(j) for all the loci j that belong to each stratum k, represented by the symbol.

$$\sum_{par(j)=k} H(j)$$

Allowing for separate counts for forward and reverse reads, and defining K' as the set of reverse positions where par(j) =k, and M' as the mask in the reverse direction, then the expected count E(count) for one stratum k, E(count|k), is a function F1 of Hf(j), Hr(j), |K\M| and |K'\M'| for all j in the stratum, as given by Equation 1.

$$E(\text{count}|k)=F1[|K\backslash M|, |K'\backslash M'|, \Sigma_{par(j)=k}Hf(j)+Hr(j)] \quad (1)$$

Any function that measures the deviation of the sum from the size of the two sets based on the target sequence can be used to express the expected count and show the variation of that deviation among different strata k. For example, in an illustrated embodiment, the observed counts are normalized by the counts in the target, and Equation 2 is used.

$$E(\text{count} \mid k) = \frac{\left[\sum_{par(j)=k} \{Hf(j) + Hr(j)\}\right]}{[|K\backslash M| + |K'\backslash M'|]} \quad (2)$$

In some embodiments, the deviation is expressed as a difference, and Equation 3 is used.

$$E(\text{count}|k)=\Sigma_{par(j)=k}[Hf(j)+Hr(j)]-|K\backslash M|-|K'\backslash M'| \quad (3)$$

In some embodiments, M' is identical to M. When strand specific partitions are not used, Hr and |K'\M'| terms are omitted in both equations 1 and 2.

Thus, step 415 determines the expected count due to bias based on: the raw counts H(j) of each locus j belonging to that stratum, k, in sample; and, the total number, k, of loci belonging to that stratum, k, in the target for each strand. The result of step 415 is an estimate of the variation of count with partition due to natural/measurement/processing system count bias.

In FIG. 5, step 415 is shown as using the target strata data in data structure 513 and the counts at each locus in forward and reverse reads in data structures 503a and 503b, respectively, to produce expected count data in data structure 515. Each data field in data structure 515 indicates the expected count (e.g., determined by Equation 1, Equation 2 or Equation 3) for one stratum. Labels "E(strata 1)," "E(Strata 2)" and "E(Strata |P|)" are inserted to indicate the fields holding data that indicates the expected counts E(count|1), E(count|2) and E(count||Pi|), respectively, in the first two and the last strata of the partition. Recall that the expected count is a measure of the deviation in count from the target strata due to count bias.

Returning to FIG. 4, in step 417, the expected counts in each stratum, E(count|k) is used to correct the counts based on the H(j) for each of T target sequence bins in the region of interest (ROI). Thus the raw counts and deviations due to bias are used to generate adjusted bin counts At. These adjustments are based on much finer scale bias determinations, as fine as one per locus in bin, than has been performed to our knowledge before this. A copy number estimate per bin b, EstCN(b) is determined as a function F2 of the counts at the loci in the bin, expressed as H(j) for j in bin b, and the deviations given by the expected counts for those loci, as given by Equation 4.

$$\text{EstCN}(t)=F2\ [\Sigma_{all\ j\ in\ t}H(j),\ \Sigma_{all\ j\ in\ t}E(\text{count}|par(j))] \quad (4)$$

In some embodiments, the differences due to biases are used by subtracting those differences from the term $\Sigma_{all\,j\,in\,t} H(j)$. In some embodiments, EstCN can be scaled to have nominal (normal) copy number equal to 2, corresponding to the actual number of copies in diploid organisms, or 1 or some other value for purely relative abundances. For example, in an illustrated embodiment defining expected count using Equation 2, the expected count is divided by the actual count as given in equation 5.

$$EstCN(t) = \frac{\sum_{all\,j\,in\,t} H(j)}{\sum_{all\,j\,in\,t} E(count\,|\,par(j))} \quad (5)$$

In some embodiments, EstCN is formulated with pseudo counts to control variance at small values by adding a constant, e.g., 1, to both numerator and denominator, as in Equation 6.

$$EstCN(t) = \frac{\left[1 + \sum_{all\,j\,in\,t} H(j)\right]}{\left[1 + \sum_{all\,j\,in\,t} E(count\,|\,par(j))\right]} \quad (6)$$

In FIG. 5, step 417 is shown as using the target strata data in data structure 513 and the expected counts in each stratum to determine the expected counts at each locus in data structure 517. Three fields in the data structure 517 are labeled by the elements of an array of expected counts at each locus j, E(count|j), represented in FIG. 5 as E(base j) corresponding to those fields, including the first two fields, E(base 1) and E(base 2), and the last field, E(N). Step 417 also combines the raw counts at each locus in forward and reverse reads in data structures 503a and 503b, respectively, and the expected counts at each locus in data structure 517 to produce estimated copy number in each bin, EstCN(t), data in data structure 520. Each data field in data structure 520 indicates the estimated copy number (e.g., determined by Equation 4, Equation 5 or Equation 6) for one bin. Labels "CN(bin 1)," and "CN(bin B)" are inserted to indicate the fields holding data that indicates the estimated copy numbers EstCN(1) and EstCN(T) in the first and the last bin of the regions of interest (ROI).

In some embodiments, a single partitioning scheme P is not used. Instead multiple partitioning schemes, called partitions, are used. In some embodiments, multiple partitions are used because there are several biases operating simultaneously, e.g., the % GC bias accounts for much of the count biases but count bias is also introduced by other lesser effects, such as number of repeats of AT sequences, contiguous or otherwise, in a window. In some embodiments, one or more desirable partitions are not known, and various trial partitions are employed. In some of these embodiments using multiple partitions, the estimated copy number from several different partitions are combined, with the contribution from each partition weighted such that the sum of the weights is a known constant, such as 1. In some of these embodiments, the weight applied to each estimated copy number is the probability of that partition or the percent of the total bias explained by that partition.

Returning to FIG. 4, in step 419, the estimated copy number is weighted by the probability of the partition used to generate the estimate. When probability is used, the sum of the probabilities of all the partitions combined is 1. When there is only one partition being used, the weight is 1. The weight or probability for each partition can be obtained in any manner. In various embodiments, the weights are determined manually or are retrieved form one or more data structures, as described above in step 401 for the target reference data. In some embodiments, step 419 includes determining the weight or probability of the partition by computations as suggested below based on data in one or more data structures.

For example, in some embodiments, the determination of expected counts due to bias can be used to discover meaningful partitions. In these embodiments, the weight or probability for the partition is based on the behavior of the expected counts with changes in strata. If the partition meaningfully reflects measurement bias, then the expected counts should vary smoothly between adjacent strata, as depicted in FIG. 3A through FIG. 3C if strata were defined by 5% bins of % GC content. In some embodiments, the results from a particular partition are compared to the known copy numbers of strands in a training set, and partitions that give good results compared to the training seta are given higher probability than partitions that do not.

In step 421, it is determined whether there is another partitioning scheme to use. If so, control passes back to step 411 and following steps to determine the next partitioning scheme and use it. If not, control passes to step 423.

In step 423, it is determined whether the estimated copy number indicates the presence of a non-normal state. In some embodiments, this determination is based on further processing of the estimated copy numbers, e.g., in a statistical model of the conditions being searched for.

If it is determined in step 423 that the presence of a non-normal state is not indicated, then in step 431 it is determined that the conditions of interest likely has not occurred in the subject. In step 433 the subject is treated as if the condition has not occurred. For example, the information is presented on a display and conveyed to the subject.

If, however, it is determined in step 423 that the presence of a non-normal state is indicated, then in step 441 it is determined that the conditions of interest likely has indeed occurred in the subject. In step 443, the condition of interest is treated by any method known for the condition of interest. For example, the information is presented on a display and conveyed to the subject, and a treatment plan is presented, or the treatment is begun, or some combination.

Using the method 400, a small amount of extracellular DNA indicative of the condition of interest can be detected in a sample with much DNA not indicative of such a condition. Both the sensitivity and accuracy are improved, as will be demonstrated in the following particular embodiments.

2. EXAMPLE EMBODIMENTS

Three example embodiments using some or all of the method 400 of FIG. 4 on DNA sequence data are described here.

2.1 GC Correction at the Base Level with Single-End Sequencing

Many non-invasive pre-natal diagnosis (NIPD) applications directly sequence the shed fragments floating in the blood of a pregnant woman. The statistical distribution of the size of these fragments has been measured, e.g., by Yu et al 2014, and are plotted in FIG. 6. FIG. 6 is a graph that illustrates example cell-free DNA fragment size for which bias is to be determined, according to an embodiment. The horizontal axis indicates fragment size in numbers of nucleotide bases (also called base pairs and abbreviated "bp" when referring to double stranded DNA). The vertical axis indicates frequency of occurrence of a fragment of a given length in percent. The two traces indicate the results in two samples, one with 10% fetal content and the other with 20% fetal content, respectively. There is a pronounced peak in fragment size frequency between 160 and 180 nucleotide bases.

Figure 6:
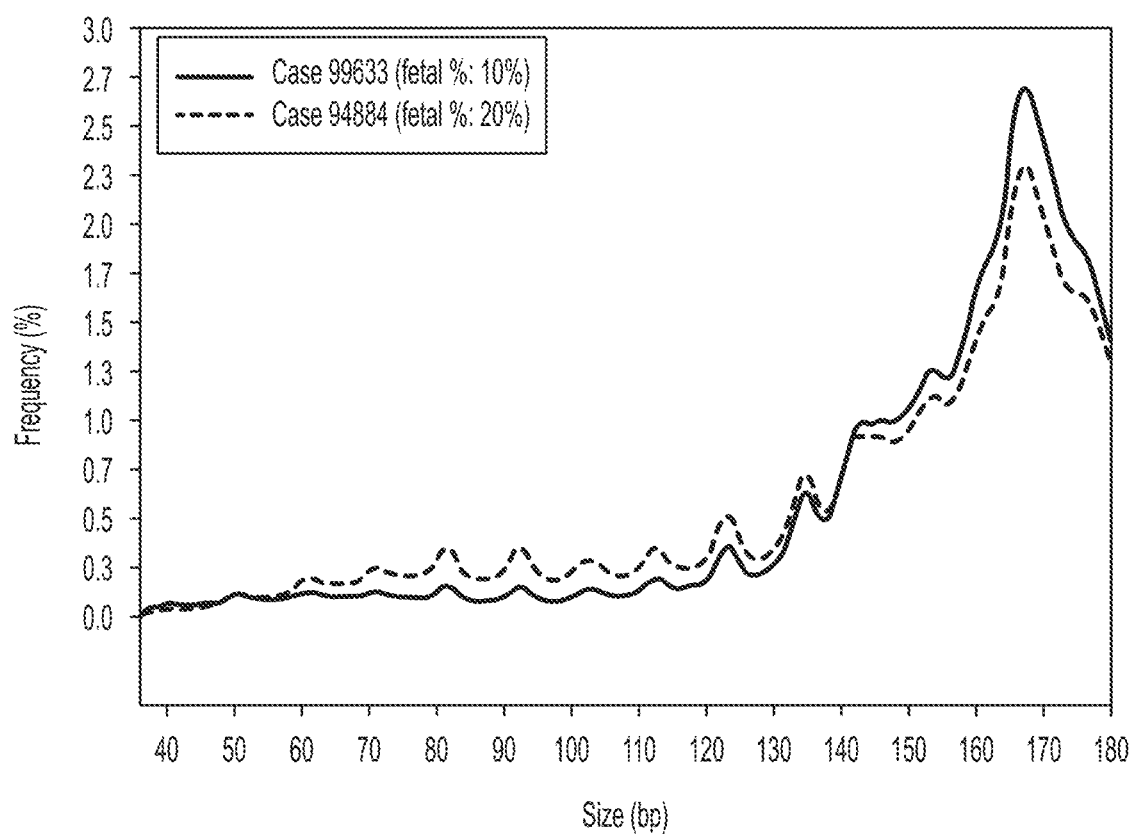
FIG. 6 is a graph that illustrates example cell-free DNA fragment size for which bias is to be determined, according to an embodiment.

Combining information about fragment size from FIG. 6 with the fact that the sequenced reads in NIPD applications are one-sided, sampled from the 5' end of fragments, an embodiment of the general method 400 is configured as described here. The partition Pi is defined in step 411 based on a window Ri of size Li, where Li indicates a number of bases and is different for each partitioning scheme. The window for locus j, Rij, starts at locus j, rather than being centered on the locus or having any other relative position. The stratum of the window is given by the integer function, floor of the % GC in Rij, represented as floor(% GC of Rij) for both forward and reverse strands. The partition window is set to the full fragment size.

The probability pr(Pi) of the partition is set, for example in step 419, to approximate the shape of the best known fragment length distribution. For example, in an illustrated embodiment, pr(Pi) is determined based on a beta distribution with the two shape parameters set to closely match the distribution in FIG. 6. Thus the most probable Pi has Li in a range from about 160 to about 180 bases. Another example would be to just use a single, most likely, fragment size, e.g., 160 bases, and set pr(Pi)=1 for Li=160 and pr(Pi)=0 for Li not equal to 160. It is advantageous to select 160 rather than 170 or 180 because selecting the lower bound of the range increases the number of available reads to populate the window R. This approach assumes the fragment starts could be biased based on the nucleotide content, specifically the % GC, in the fragment.

Figure 7:
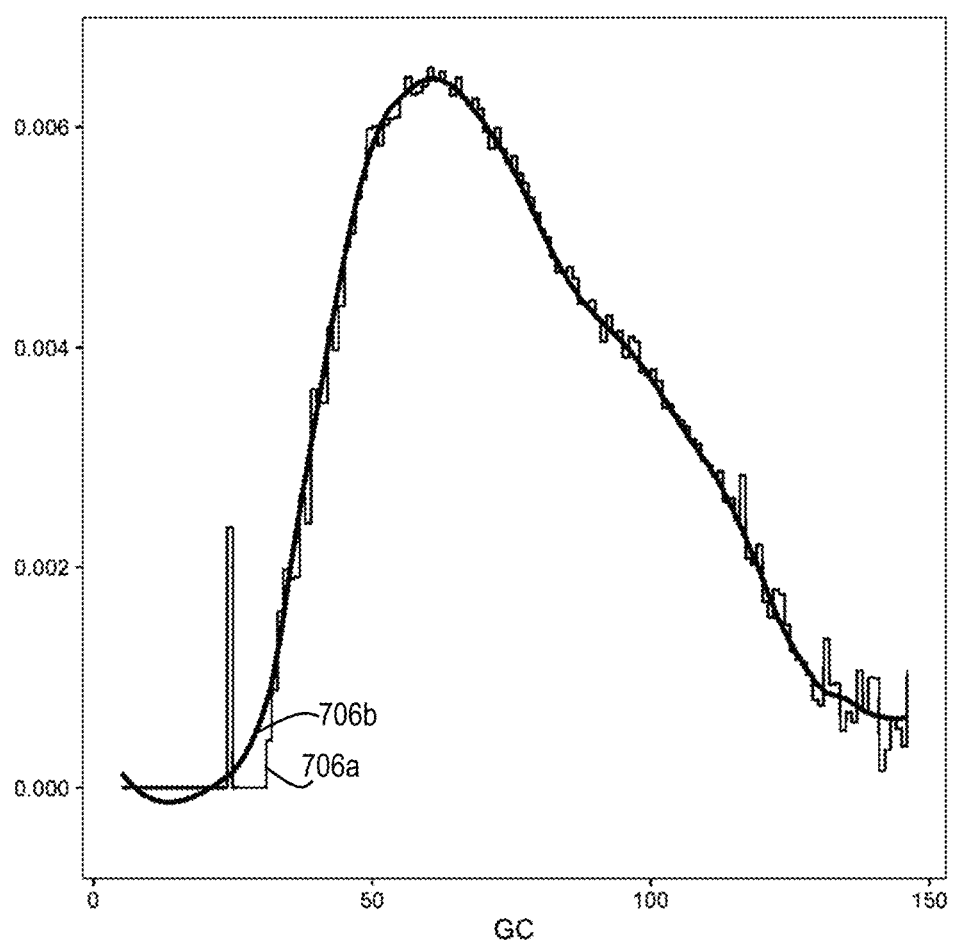
FIG. 7 is a graph that illustrates an example expected count bias based on GC content in fine grained window of 160 bases starting at any locus, according to an embodiment.

FIG. 7 is a graph that illustrates an example expected count bias based on GC content in fine grained window of 160 bases starting at any locus, according to an embodiment. The horizontal axis indicates the GC count in windows of 160 bases (each count defines a % GC which is a stratum. The vertical axis indicates the expected number of generated sequences aligned to genomic positions of that stratum as stored in data structure 515 that results from step 415 of the method 400. As can be seen, loci with 160-base windows having low GC content (less than about 40/160=25%) and high GC content (greater than about 120/160=75%) are under-covered, i.e., are biased low. Every window of different GC content is biased differently compared to a random distribution over the target sequence. The stepped trace indicates the estimated counts and can be used to correct the counts obtained at each locus during computation of the estimated copy number for each bin. Alternatively, the smooth trace can be fit to the stepped trace and the smoothed trace used to correct the counts obtained at each locus during computation of the estimated copy number for each bin.

Figure 8:
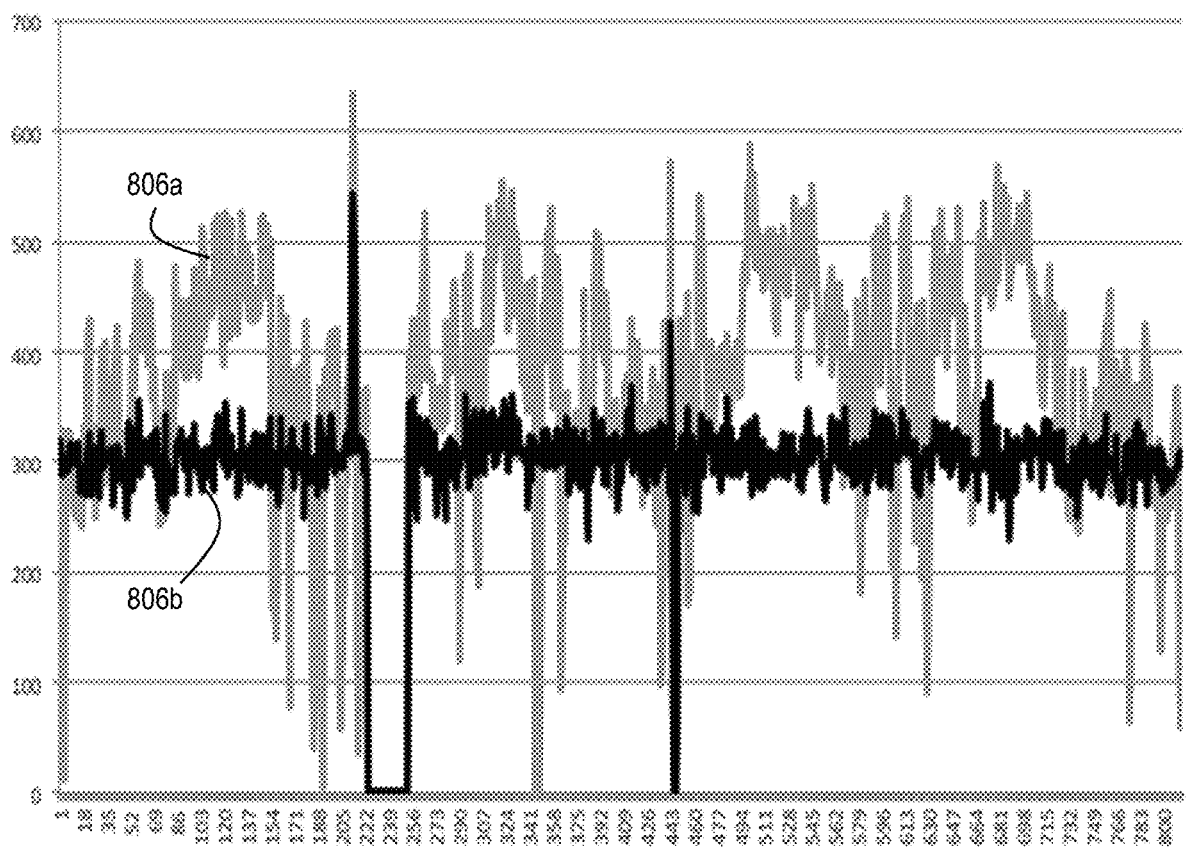
FIG. 8 Is a graph that illustrates example original bin scores for bins of 100 kilobases compared to corrected bin scores for bins of the same size using the fine grained count bias, according to an embodiment.

FIG. 8 Is a graph that illustrates example original bin scores for bins of 100 kilobases compared to corrected bin scores for bins of the same size using the fine grained count bias, according to an embodiment. The horizontal axis indicates bin number. There are 800 such bins representing 80 million loci on chromosome 17 of the human genome. The vertical axis indicates the difference between the observed count, $\Sigma_{all\ j\ in\ t} H(j)$, and expected count, $\Sigma_{all\ j\ in\ t} E(count|par(j))$, re-centered to the average observed bin count of about 300. This difference affects, but is different from, the estimated copy number. The variability of trace 806a is much reduced in trace 806b. This is a powerful indication that the much of the variability of 806a is explained by the count bias due to % GC content in the 160 base windows of the partition.

Figure 9:
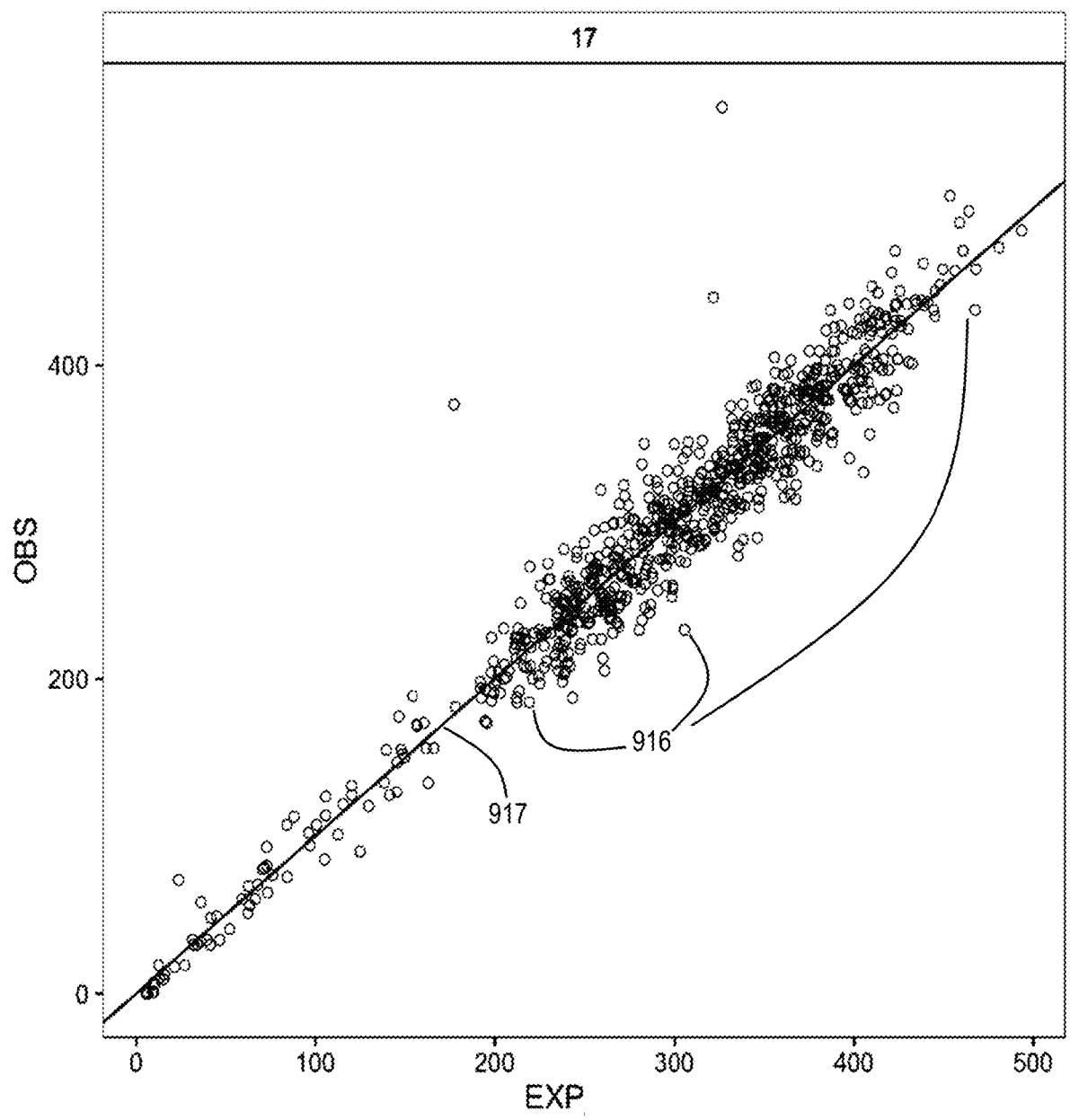
FIG. 9 is a graph that illustrates example relationship between observed bin counts and bin counts expected based on fine scale count bias, according to another embodiment.

FIG. 9 is a graph that illustrates example relationship between observed bin counts and bin counts expected based on fine scale count bias, according to another embodiment. The horizontal axis indicates expected count in the bin, $\Sigma_{all\ j\ in\ t} E(count|par(j))$. The vertical axis indicates the observed count in the bin, $\Sigma_{all\ j\ in\ t} H(j)$. Bin size is 100 kilobases and bins are from a single sample over Human chromosome 17, for which there are about 800 bins. The individual bin results are indicated by open circles 916, and the line 917 indicates perfect agreement, e.g., y=x. The data show the same number of copies of chromosome 17 as would be expected if there were no copy number variation (CNV).

2.2 GC Correction at the Base Level with Paired-End Sequencing

Another embodiment has pr(Pi) being estimated from information in a paired-end sequencing run. In this embodiment, instead of relying on the probability of fragment size distributions from an independent source, the fragment sizes are deduced from the distance between the paired end reads.

As in section 2.1, the partition Pi is defined in step 411 based on a window Ri of size Li, where Li indicates a number of bases and is different for each partitioning scheme. The window for locus j, Rij, starts at locus j, rather than being centered on the locus or having any other relative position. The stratum of the window is given by floor (% GC of Rij) for both forward and reverse strands.

Unlike section 2.1, pr(Pi) is set by using a distribution estimated from the fragment sizes inferred from the distance between mapped 5' and 3' read. For example, the Li is set to the fragment size in the middle or lower end of every 5 percentile values in the observed fragment size distribution and given a probability of 5%.

2.3 Correcting for GC and Base Fragmentation Probability

In another embodiment, it is anticipated that the distribution of reads is influenced by the base content to the left of the locus j as well as the fragment size. Thus in this embodiment, the partitioning is done by GC of the anticipated fragment size and also by the base content in a more immediate vicinity on either side of the locus j.

Figure 12:
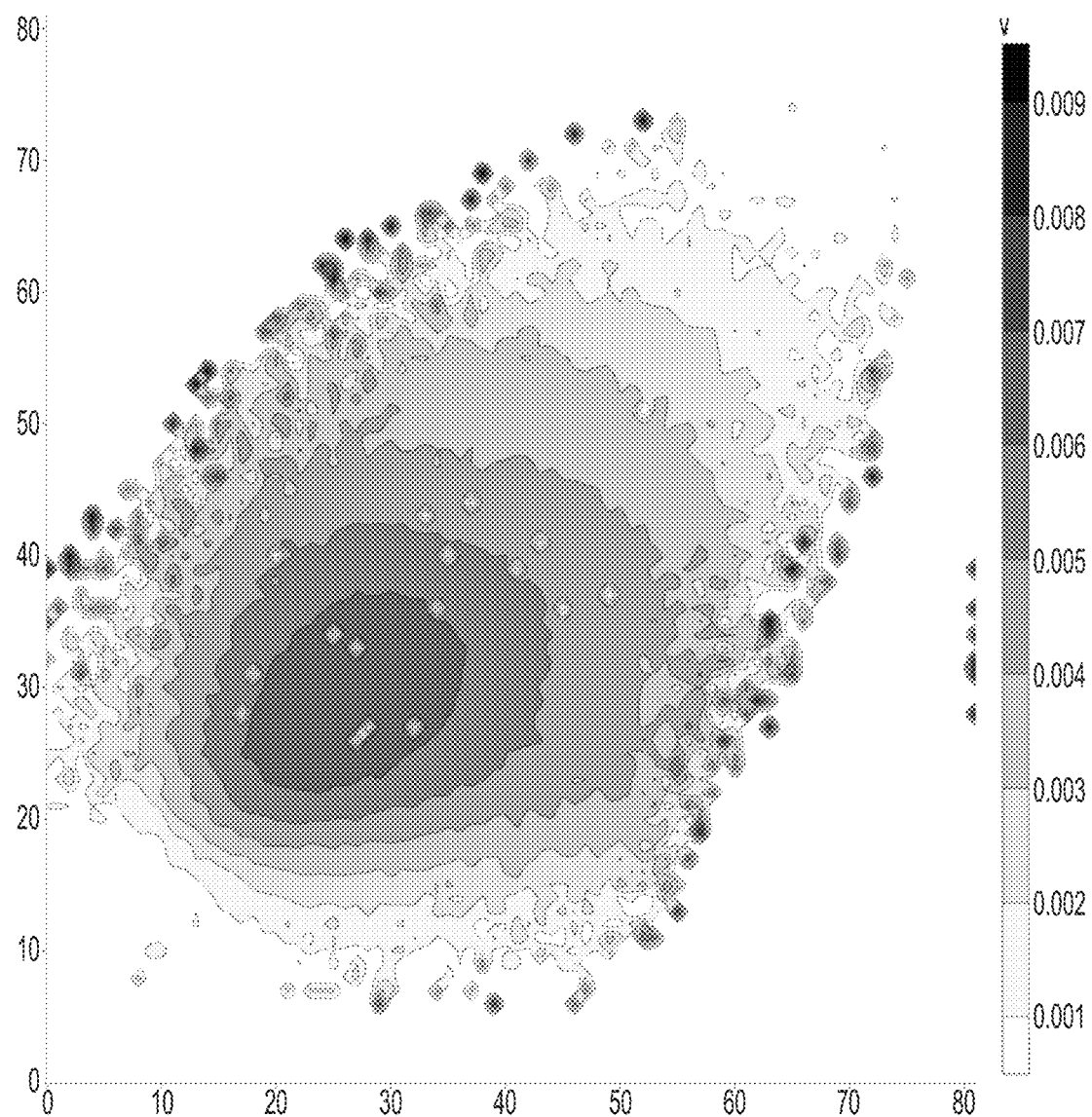
FIG. 12 is a contour plot that depicts the relative counts in each two dimensional stratum of a two dimensional partition, according to an embodiment.

In this embodiment, for each of the forward strand and the reverse strand, with anticipated read length r, two windows R1i and R2 are defined for each Partition, Pi. Window R1i has size Li+r, where Li is defined as above, and starts at locus j. Window R2 has size equal to 2r+1 centered on locus j. Note that R2 is independent of partition index i. The stratum of the window is two dimensional with one dimension given by f1(j)=floor(% GC of R1ij) and the other given by the f2(j)=floor (% GC of R2j), for both forward and reverse strands. Then, the stratum par(j) is given by the two dimensional vector (f1(j), f2(j)). FIG. 12 is a contour plot that depicts the relative counts in each two dimensional stratum of a two dimensional partition, according to an embodiment. In this embodiment, one dimension is based on one window in the vicinity of the locus j and the other dimension is based on a different window in the vicinity of the locus j. The axis for each dimension indicates the % GC content in the window. Each stratum is a small two dimensional box on this plot identified by x,y coordinates associated with a box, e.g., the x,y coordinates at a corner or center of the box. The value at each box is the relative count for that two dimensional stratum, e.g., the expected number of generated sequences aligned to genomic positions of that stratum as stored in data structure 515 that results from step 415 of the method 400. Values for all strata are indicated by contour lines and shaded areas, where darker shading indicates a higher relative count. As can be seen, strata with % GC content in the 20 to 40% range in both dimensions have the highest counts. Higher and lower GC content strata are biased low. In other embodiments, the different dimensions of one partition are contents of different bases rather the same bases in different window sizes, in addition to or instead of changes in window sizes. In some embodiments, a single partition has more than two dimensions.

These embodiments demonstrate a system and method for non-invasive diagnosis of DNA signals in a sample which corrects for GC and other factors at the individual base level. This method can be run at the individual sample level so that large numbers of samples are not needed to apply the method. In addition, this method corrects for biases invisible at the bin level. The method can be used by itself to detect low fetal fraction CNVs or as a pre-processing variance reduction step for existing bin level CNV NIPD systems, among others.

3. COMPUTATIONAL HARDWARE OVERVIEW

Figure 10:
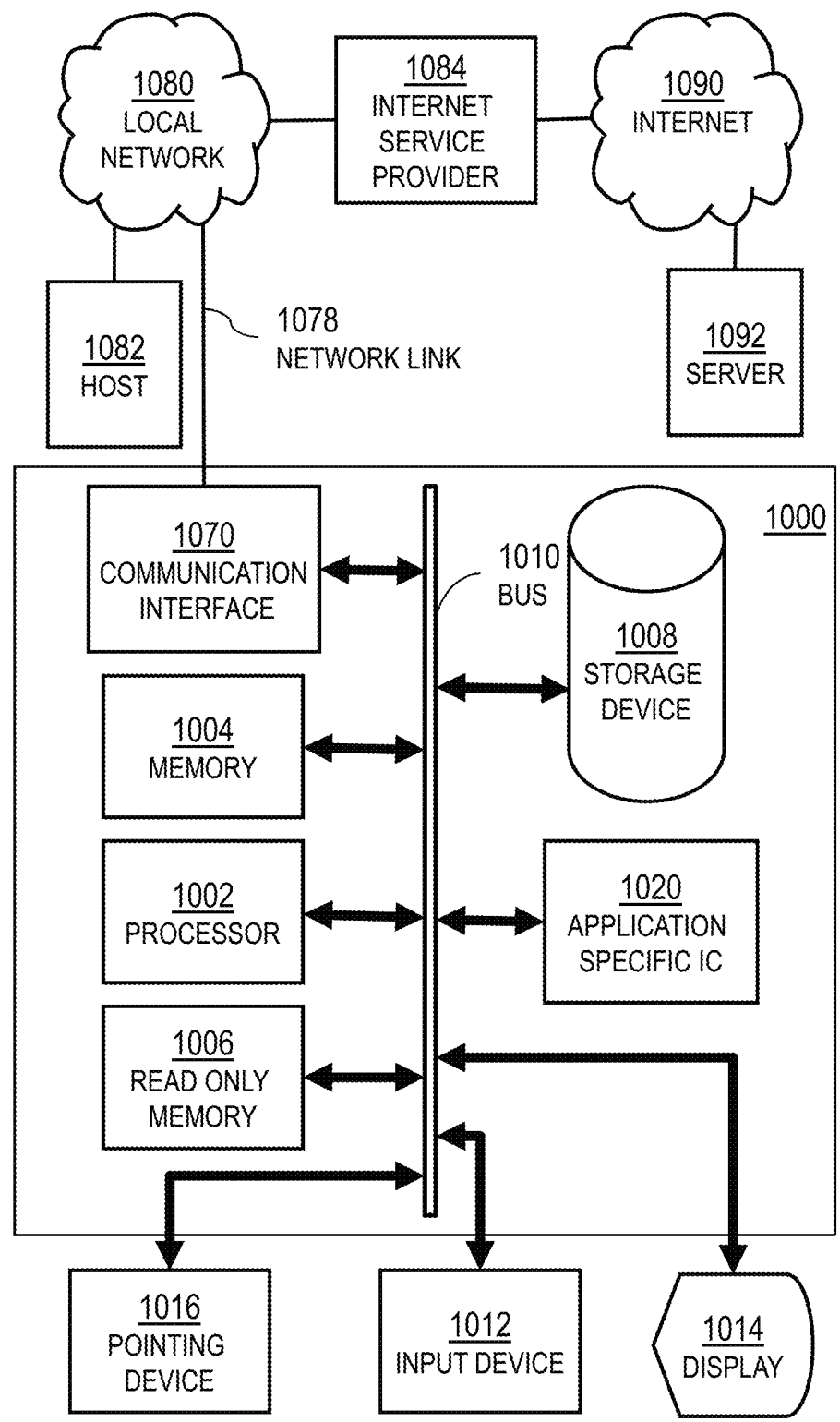
FIG. 10 is a block diagram that illustrates a computer system upon which an embodiment of the invention may be implemented.

FIG. 10 is a block diagram that illustrates a computer system 1000 upon which an embodiment of the invention may be implemented. Computer system 1000 includes a communication mechanism such as a bus 1010 for passing information between other internal and external components of the computer system 1000. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1000, or a portion thereof, constitutes a means for performing one or more steps of one or more methods described herein.

A sequence of binary digits constitutes digital data that is used to represent a number or code for a character. A bus 1010 includes many parallel conductors of information so that information is transferred quickly among devices coupled to the bus 1010. One or more processors 1002 for processing information are coupled with the bus 1010. A processor 1002 performs a set of operations on information. The set of operations include bringing information in from the bus 1010 and placing information on the bus 1010. The set of operations also typically include comparing two or more units of information, shifting positions of units of information, and combining two or more units of information, such as by addition or multiplication. A sequence of operations to be executed by the processor 1002 constitutes computer instructions.

Computer system 1000 also includes a memory 1004 coupled to bus 1010. The memory 1004, such as a random access memory (RAM) or other dynamic storage device, stores information including computer instructions. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of computer instructions. The computer system 1000 also includes a read only memory (ROM) 1006 or other static storage device coupled to the bus 1010 for storing static information, including instructions, that is not changed by the computer system 1000. Also coupled to bus 1010 is a non-volatile (persistent) storage device 1008, such as a magnetic disk or optical disk, for storing information, including instructions, that persists even when the computer system 1000 is turned off or otherwise loses power.

Information, including instructions, is provided to the bus 1010 for use by the processor from an external input device 1012, such as a keyboard containing alphanumeric keys operated by a human user, or a sensor. A sensor detects conditions in its vicinity and transforms those detections into signals compatible with the signals used to represent information in computer system 1000. Other external devices coupled to bus 1010, used primarily for interacting with humans, include a display device 1014, such as a cathode ray tube (CRT) or a liquid crystal display (LCD), for presenting images, and a pointing device 1016, such as a mouse or a trackball or cursor direction keys, for controlling a position of a small cursor image presented on the display 1014 and issuing commands associated with graphical elements presented on the display 1014.

In the illustrated embodiment, special purpose hardware, such as an application specific integrated circuit (IC) 1020, is coupled to bus 1010. The special purpose hardware is configured to perform operations not performed by processor 1002 quickly enough for special purposes. Examples of application specific ICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a two-way communication coupling to a variety of external devices that operate with their own processors, such as printers, scanners and external disks. In general the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1070 sends and receives electrical, acoustic or electromagnetic signals, including infrared and optical signals that carry information streams, such as digital data.

The term computer-readable medium is used herein to refer to any medium that participates in providing information to processor 1002, including instructions for execution. Such a medium may take many forms, including, but not limited to, non-volatile media, volatile media and transmission media. Non-volatile media include, for example, optical or magnetic disks, such as storage device 1008. Volatile media include, for example, dynamic memory 1004. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1002, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1002, except for carrier waves and other signals.

Logic encoded in one or more tangible media includes one or both of processor instructions on a computer-readable storage media and special purpose hardware, such as ASIC 1020.

Network link 1078 typically provides information communication through one or more networks to other devices that use or process the information. For example, network link 1078 may provide a connection through local network 1080 to a host computer 1082 or to equipment 1084 operated by an Internet Service Provider (ISP). ISP equipment 1084 in turn provides data communication services through the public, world-wide packet-switching communication network of networks now commonly referred to as the Internet 1090. A computer called a server 1092 connected to the Internet provides a service in response to information received over the Internet. For example, server 1092 provides information representing video data for presentation at display 1014.

The invention is related to the use of computer system 1000 for implementing the techniques described herein. According to one embodiment of the invention, those techniques are performed by computer system 1000 in response to processor 1002 executing one or more sequences of one or more instructions contained in memory 1004. Such instructions, also called software and program code, may be read into memory 1004 from another computer-readable medium such as storage device 1008. Execution of the sequences of instructions contained in memory 1004 causes processor 1002 to perform the method steps described herein. In alternative embodiments, hardware, such as application specific integrated circuit 1020, may be used in place of or in combination with software to implement the invention. Thus, embodiments of the invention are not limited to any specific combination of hardware and software.

The signals transmitted over network link 1078 and other networks through communications interface 1070, carry information to and from computer system 1000. Computer system 1000 can send and receive information, including program code, through the networks 1080, 1090 among others, through network link 1078 and communications interface 1070. In an example using the Internet 1090, a server 1092 transmits program code for a particular application, requested by a message sent from computer 1000, through Internet 1090, ISP equipment 1084, local network 1080 and communications interface 1070. The received code may be executed by processor 1002 as it is received, or may be stored in storage device 1008 or other non-volatile storage for later execution, or both. In this manner, computer system 1000 may obtain application program code in the form of a signal on a carrier wave.

Various forms of computer readable media may be involved in carrying one or more sequence of instructions or data or both to processor 1002 for execution. For example, instructions and data may initially be carried on a magnetic disk of a remote computer such as host 1082. The remote computer loads the instructions and data into its dynamic memory and sends the instructions and data over a telephone line using a modem. A modem local to the computer system 1000 receives the instructions and data on a telephone line and uses an infra-red transmitter to convert the instructions and data to a signal on an infra-red a carrier wave serving as the network link 1078. An infrared detector serving as communications interface 1070 receives the instructions and data carried in the infrared signal and places information representing the instructions and data onto bus 1010. Bus 1010 carries the information to memory 1004 from which processor 1002 retrieves and executes the instructions using some of the data sent with the instructions. The instructions and data received in memory 1004 may optionally be stored on storage device 1008, either before or after execution by the processor 1002.

Figure 11:
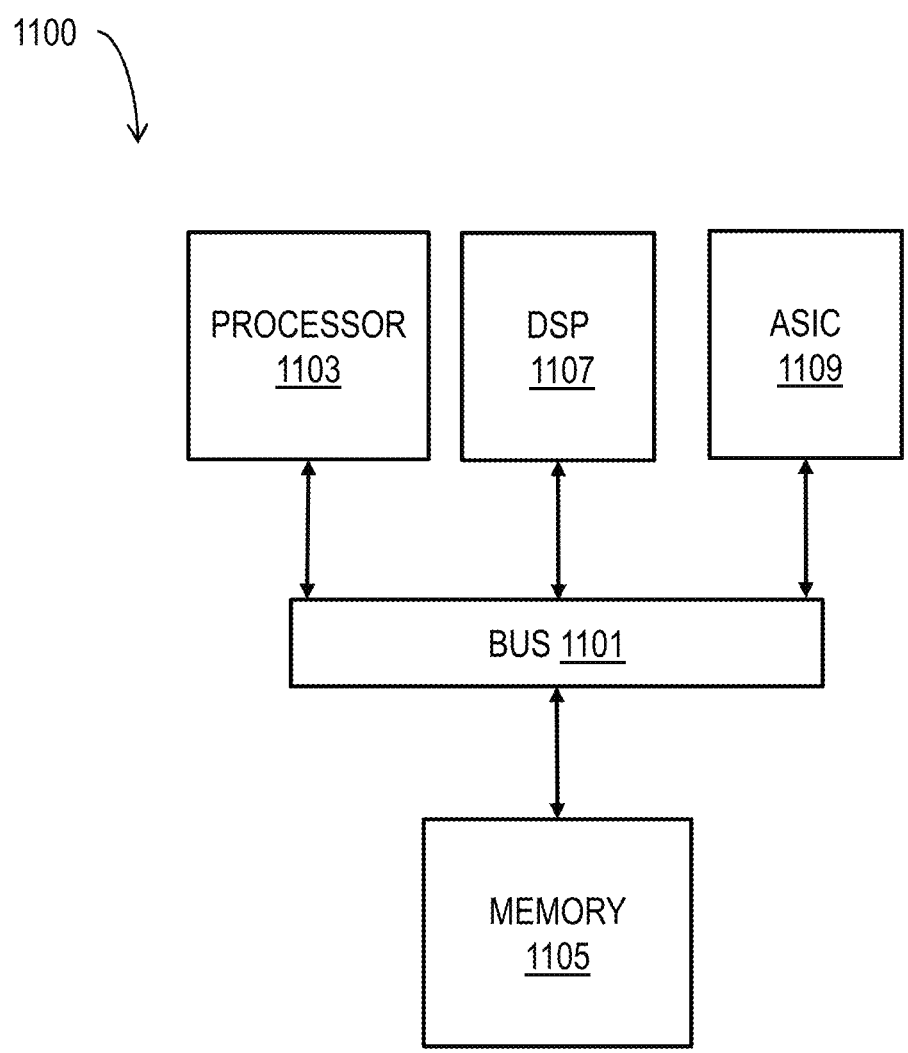
FIG. 11 is a block diagram that illustrates a chip set upon which an embodiment of the invention may be implemented.

FIG. 11 illustrates a chip set 1100 upon which an embodiment of the invention may be implemented. Chip set 1100 is programmed to perform one or more steps of a method described herein and includes, for instance, the processor and memory components described with respect to FIG. 10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1100, or a portion thereof, constitutes a means for performing one or more steps of a method described herein.

In one embodiment, the chip set 1100 includes a communication mechanism such as a bus 1101 for passing information among the components of the chip set 1100. A processor 1103 has connectivity to the bus 1101 to execute instructions and process information stored in, for example, a memory 1105. The processor 1103 may include one or more processing cores with each core configured to perform independently. A multi-core processor enables multiprocessing within a single physical package. Examples of a multi-core processor include two, four, eight, or greater numbers of processing cores. Alternatively or in addition, the processor 1103 may include one or more microprocessors configured in tandem via the bus 1101 to enable independent execution of instructions, pipelining, and multithreading. The processor 1103 may also be accompanied with one or more specialized components to perform certain processing functions and tasks such as one or more digital signal processors (DSP) 1107, or one or more application-specific integrated circuits (ASIC) 1109. A DSP 1107 typically is configured to process real-world signals (e.g., sound) in real time independently of the processor 1103. Similarly, an ASIC 1109 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1103 and accompanying components have connectivity to the memory 1105 via the bus 1101. The memory 1105 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1105 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

4. REFERENCES

All references cited herein are hereby incorporated by reference in their entirety as if fully set for the herein, except for terminology that is inconsistent with that used herein.

Chen, S., et al. "A method for noninvasive detection of fetal large deletions/duplications by low coverage massively parallel sequencing," Prenatal Diagnosis, 2013, Page(s): 584-590, Vol. 33

Fan, H. C., et al., "Sensitivity of Noninvasive Prenatal Detection of Fetal Aneuploidy from Maternal Plasma Using Shotgun Sequencing Is Limited Only by Counting Statistics," PLoS ONE, 2010, Page(s): 1-7, Vol. 5, Issue 5, e10439

Lo, K. K., et al., "Limited Clinical Utility of Non-invasive Prenatal Testing for Subchromosomal Abnormalities," The American Journal of Human Genetics, 2016, Page(s): 34-44, Vol. 98

Ross, M. G., et al., "Characterizing and measuring bias in sequence data," Genome Biology, 2013, Page(s): 1-20, Vol. 14, No. R51

Sehnert, A. J., et al., "Optimal Detection of Fetal Chromosomal Abnormalities by Massively Parallel DNA Sequencing of Cell-Free Fetal DNA from Maternal Blood," Clinical Chemistry, 2011, Page(s): 1042-1049, Vol. 57, Issue 7

Yu, S. C. Y., et al., "Noninvasive Prenatal Molecular Karyotyping from Maternal Plasma," PLoS ONE, 2013, Page(s): 1-8, Vol. 8, Issue 4, e60968

Yua, S. C. Y., et al., "Size-based molecular diagnostics using plasma DNA for noninvasive prenatal testing," PNAS, Jun. 10, 2014, Page(s): 8583-8588, Vol. 111, No. 23

Zhao, C., et al., "Detection of Fetal Subchromosomal Abnormalities by Sequencing Circulating Cell-Free DNA from Maternal Plasma," Clinical Chemistry, 2015, Page(s): 608-616 Vol. 61, Issue 4

The American Heritage® Dictionary of Student Science, Second Edition. Copyright© 2014 by Houghton Mifflin Harcourt Publishing Company. Published by Houghton Mifflin Harcourt Publishing Company. All rights reserved.

Feller, William 1966. An Introduction To Probability Theory and Its Applications. Wiley

What is claimed is:

1. A method executed on a processor comprising:
   a. obtaining first data that indicates a target sequence of nucleic acid bases at a plurality of loci, wherein the target sequence comprises a plurality of bins of loci for which a relative abundance among the bins is indicative of a condition of interest and a bin size is on an order of thousands to millions of loci;
   b. obtaining second data that indicates alignment with the target sequence of thousands to millions of reads of DNA fragments in a sample from a subject wherein read lengths are hundreds of nucleotides;
   c. determining a raw count $H_j$ of reads that start at each locus j;
   d. obtaining partition data that indicates, for a first partition, a window comprising a number of bases less than a number of loci in a bin and position relative to a current locus, and a plurality of strata based on a corresponding plurality of different contents of nucleic acid bases in the window;
   e. attributing to each locus j in the target sequence a stratum k(j) of the plurality of strata of the first partition based on the content of nucleic acid bases in the target sequence in the window relative to the locus j;
   f. determining an expected count of each stratum, E(k), in the first partition based on the raw counts $H_j$ of each locus j belonging to the stratum k and a total number of loci in the target sequence belonging to the stratum k;
   g. determining a copy number of a first bin based on a sum over all loci in the first bin of E(k(j)) for the first partition; and h. presenting on a display, output data that indicates condition of the subject based at least in part on the copy number of the first bin.

2. A method as recited in claim 1, wherein:
the method further comprises i) determining a copy number of a second bin based on a sum over all loci in the second bin of $E(k(j))$ for the first partition; and
the condition of the subject is based also at least in part on the copy number of the second bin.

3. A method as recited in claim 1, wherein:
the method further comprises repeating steps d and e and f for a second partition different from the first partition; and
determining the copy number of the first bin further comprises determining the copy number of the first bin based on the sum over all loci in the first bin of $E(k(j))$ for the first partition weighted by a probability of the first partition and a sum over all loci in the first bin of $E(k(j))$ for the second partition weighted by a probability of the second partition.

4. A method as recited in claim 1, wherein obtaining partition data further comprises obtaining partition data that indicates, for the first partition, two windows, a first window comprising a first number of bases less than a number of loci in a bin and a first position relative to the current locus, and a second window comprising a second number of bases less than a number of loci in a bin and a second position relative to the current locus, wherein the second number of bases is different from the first number of bases or the second position is different from the first position or both, and the partition data further indicates a plurality of strata based on a corresponding plurality of different contents of nucleic acid bases in the two windows.

5. A method as recited in claim 1, further comprising determining in the second data which positions are never covered and adding those positions into a mask of loci excluded from the target sequence.

6. A non-transitory computer-readable medium carrying one or more sequences of instructions, wherein execution of the one or more sequences of instructions by one or more processors causes the one or more processors to perform the following:
a. obtain first data that indicates a target sequence of nucleic acid bases at a plurality of loci, wherein the target sequence comprises a plurality of bins of loci for which a relative abundance among the bins is indicative of a condition of interest and a bin size is on an order of thousands to millions of loci;
b. obtain second data that indicates alignment with the target sequence of thousands to millions of reads of DNA fragments in a sample from a subject wherein read lengths are hundreds of nucleotides;
c. determine a raw count $H_j$ of reads that start at each locus j;
d. obtain partition data that indicates, for a first partition, a window comprising a number of bases less than a number of loci in a bin and position relative to a current locus, and a plurality of strata based on a corresponding plurality of different contents of nucleic acid bases in the window;
e. attribute to each locus j in the target sequence a stratum $k(j)$ of the plurality of strata of the first partition based on the content of nucleic acid bases in the target sequence in the window relative to the locus j;
f. determine an expected count of each stratum, $E(k)$, in the first partition based on the raw counts $H_j$ of each locus j belonging to the stratum k and a total number of loci in the target sequence belonging to the stratum k;
g. determine a copy number of a first bin based on a sum over all loci in the first bin of $E(k(j))$ for the first partition; and
h. cause to be presented on a display, output data that indicates condition of the subject based at least in part on the copy number of the first bin.

7. A non-transitory computer-readable medium as recited in claim 6, wherein:
execution of the one or more sequences of instructions by the one or more processors further causes the one or more processors to i) determine a copy number of a second bin based on a sum over all loci in the second bin of $E(k(j))$ for the first partition; and
the condition of the subject is based also at least in part on the copy number of the second bin.

8. A non-transitory computer-readable medium as recited in claim 6, wherein:
execution of the one or more sequences of instructions by the one or more processors further causes the one or more processors to repeat steps d and e and f for a second partition different from the first partition; and
determine the copy number of the first bin further comprises determine the copy number of the first bin based on the sum over all loci in the first bin of $E(k(j))$ for the first partition weighted by a probability of the first partition and a sum over all loci in the first bin of $E(k(j))$ for the second partition weighted by a probability of the second partition.

9. A non-transitory computer-readable medium as recited in claim 6, wherein obtain partition data further comprises obtain partition data that indicates, for the first partition, two windows, a first window comprising a first number of bases less than a number of loci in a bin and a first position relative to the current locus, and a second window comprising a second number of bases less than a number of loci in a bin and a second position relative to the current locus, wherein the second number of bases is different from the first number of bases or the second position is different from the first position or both, and the partition data further indicates a plurality of strata based on a corresponding plurality of different contents of nucleic acid bases in the two windows.

10. A non-transitory computer-readable medium as recited in claim 6, wherein execution of the one or more sequences of instructions by the one or more processors further causes the one or more processors to determine in the second data which positions are never covered and adding those positions into a mask of loci excluded from the target sequence.

11. A system comprising:
at least one processor; and
at least one memory including one or more sequences of instructions,
the at least one memory and the one or more sequences of instructions configured to, with the at least one processor, cause the apparatus to:
a. obtain first data that indicates a target sequence of nucleic acid bases at a plurality of loci, wherein the target sequence comprises a plurality of bins of loci for which a relative abundance among the bins is indicative of a condition of interest and a bin size is on an order of thousands to millions of loci;
b. obtain second data that indicates alignment with the target sequence of thousands to millions of reads of DNA fragments in a sample from a subject wherein read lengths are hundreds of nucleotides;

c. determine a raw count Hj of reads that start at each locus j;

d. obtain partition data that indicates, for a first partition, a window comprising a number of bases less than a number of loci in a bin and position relative to a current locus, and a plurality of strata based on a corresponding plurality of different contents of nucleic acid bases in the window;

e. attribute to each locus j in the target sequence a stratum k(j) of the plurality of strata of the first partition based on the content of nucleic acid bases in the target sequence in the window relative to the locus j;

f. determine an expected count of each stratum, E(k), in the first partition based on the raw counts Hj of each locus j belonging to the stratum k and a total number of loci in the target sequence belonging to the stratum k;

g. determine a copy number of a first bin based on a sum over all loci in the first bin of E(k(j)) for the first partition; and h. cause to be presented on a display, output data that indicates condition of the subject based at least in part on the copy number of the first bin.

12. A system as recited in claim 11, wherein:

the one or more sequences of instructions are further configured to, with the at least one processor, cause the apparatus to i) determine a copy number of a second bin based on a sum over all loci in the second bin of E(k(j)) for the first partition; and the condition of the subject is based also at least in part on the copy number of the second bin.

13. A system as recited in claim 11, wherein:

the one or more sequences of instructions are further configured to, with the at least one processor, cause the apparatus to repeat steps d and e and f for a second partition different from the first partition; and determine the copy number of the first bin further comprises determine the copy number of the first bin based on the sum over all loci in the first bin of E(k(j)) for the first partition weighted by a probability of the first partition and a sum over all loci in the first bin of E(k(j)) for the second partition weighted by a probability of the second partition.

14. A system as recited in claim 11, wherein obtain partition data further comprises obtain partition data that indicates, for the first partition, two windows, a first window comprising a first number of bases less than a number of loci in a bin and a first position relative to the current locus, and a second window comprising a second number of bases less than a number of loci in a bin and a second position relative to the current locus, wherein the second number of bases is different from the first number of bases or the second position is different from the first position or both, and the partition data further indicates a plurality of strata based on a corresponding plurality of different contents of nucleic acid bases in the two windows.

15. A system as recited in claim 11, wherein the one or more sequences of instructions are further configured to, with the at least one processor, cause the apparatus to determine in the second data which positions are never covered and adding those positions into a mask of loci excluded from the target sequence.

* * * * *